United States Patent
Kang

(10) Patent No.: US 11,370,880 B1
(45) Date of Patent: Jun. 28, 2022

(54) GROWTH FACTOR-LOADED ELASTIC POLY(XYLITOL-DODECANEDIOIC ACID) POLYMER FOR TISSUE ENGINEERING

(71) Applicant: FLORIDA ATLANTIC UNIVERSITY BOARD OF TRUSTEES, Boca Raton, FL (US)

(72) Inventor: Yunqing Kang, Boca Raton, FL (US)

(73) Assignee: FLORIDA ATLANTIC UNIVERSITY BOARD OF TRUSTEES, Boca Raton, FL (US)

(*) Notice: Subject to any disclaimer, the term of this patent is extended or adjusted under 35 U.S.C. 154(b) by 240 days.

(21) Appl. No.: 16/668,978

(22) Filed: Oct. 30, 2019

Related U.S. Application Data

(60) Provisional application No. 62/752,444, filed on Oct. 30, 2018.

(51) Int. Cl.
| | | |
|---|---|---|
| C08G 63/12 | (2006.01) | |
| A61K 47/59 | (2017.01) | |
| A61K 47/34 | (2017.01) | |
| A61K 38/18 | (2006.01) | |
| C08G 63/78 | (2006.01) | |
| C08G 63/60 | (2006.01) | |
| C08G 63/91 | (2006.01) | |

(52) U.S. Cl.
CPC .............. *C08G 63/12* (2013.01); *A61K 38/18* (2013.01); *A61K 38/1825* (2013.01); *A61K 47/34* (2013.01); *A61K 47/59* (2017.08); *A61K 47/593* (2017.08); *C08G 63/78* (2013.01); *C08G 63/60* (2013.01); *C08G 63/912* (2013.01)

(58) Field of Classification Search
CPC ........ C08G 63/12; C08G 63/78; A61K 47/34; A61K 47/59; A61K 47/593; A61K 38/18; A61K 38/1825
See application file for complete search history.

(56) References Cited

U.S. PATENT DOCUMENTS

2011/0065871 A1* 3/2011 Nagano .................. C08G 63/80
525/450
2018/0296732 A1* 10/2018 Kutryk .................... A61L 27/34

OTHER PUBLICATIONS

Bruggeman, J.P., et al.; Biomaterials, 2008, vol. 29, p. 4726-4735.*
Li, Y., et al.; Biomedical Materials, 2013, vol. 8, p. 1-10.*
Albarran-Preza et al. Sweet Polymers: Synthesis and Characterization of Xylitol-Based Epoxidized Linseed Oil Resins. European Polymer Journal, 2016, 75, 539-551.
Allen et al. Drug Delivery Systems: Entering the Mainstream. Science 2004, 303, 1818-1822.
Altankov et al. Studies on the Biocompatibility of Materials: Fibroblast Reorganization of Substratum-Bound Fibronectin on Surfaces Varying in Wettability. Journal of Biomedical Materials Research. 1996, 30, 385-391.
Barbiroli et al. Polyethylene like Polymers. Aliphatic Polyesters of Dodecanedioic Acid: 1. Synthesis and Properties. Eur. Polym. J. 2003, 39, 655-661.
Beenken et al. Use of Xylitol To Enhance the Therapeutic Efficacy of Polymethylmethacrylate-Based Antibiotic Therapy in Treatment of Chronic Osteomyelitis. Antimicrobial Agents Chemotherapy 2012, 56(11), 5839-5844.
Bhaittarai et al. A Review on Properties of Natural and Synthetic Based Electrospun Fibrous Materials for Bone Tissue Engineering. Membranes 2018, 8 (62), 1-24.
Bruggeman et al. Biodegradable Xylitol-Based Elastomers: In Vivo Behavior and Biocompatibility. J. Biomed. Mater. Res. A 2010, 95A (1), 92-104.
Bruggeman et al. Biodegradable Xylitol-Based Polymers. Adv. Mater. 2008, 20, 1922-1927.
Chung et al. Glass Transition and Enthalpy Relaxation of Cross-Linked Com Starches. Carbohydr. Polym. 2004, 55, 9-15.
Costa et al. Modeling and Comparison of Dissolution Profiles. Eur. J. Pharm. Sci. 2001, 13, 123-133.
Dasgupta et al. Combinatorial Approach to Develop Tailored Biodegradable Poly(Xylitol Dicarboxylate) Polyesters. Biomacromolecules 2014, 15, 4302-4313.
Davenport Huyer et al. Highly Elastic and Moldable Polyester Biomaterial for Cardiac Tissue Engineering Applications. ACS Biomater. Sci. Eng. 2016, 2, 780-788.
Deepa et al. Synthesis and Characterisation of Certain Biodegradable Xylitol Based Polyesters. Asian J. Res. Chem. 2016, 9(12), 679-682.
Firoozi et al. Synthesis of Poly(ε-Caprolactone)-Based Polyurethane Semi-Interpenetrating Polymer Networks as Scaffolds for Skin Tissue Regeneration. Int. J. Polym. Mater. Polym. Biomater. 2017, 66(16), 805-811.
Gentile et al. An Overview of Poly(Lactic-co-Glycolic) Acid (PLGA)-Based Biomaterials for Bone Tissue Engineering. Int. J. Mol. Sci. 2014, 15, 3640-3659.
Goepferich. "Mechanisms of polymer degradation and erosion." Biomaterials 17, No. 2 (1996): 103-114.
Hawkins et al. Nonlinear Decrease of Background Fluorescence in Polymer Thin-Films—a Survey of Materials and How They Can Complicate Fluorescence Detection in μ TAS. Lab Chip, 2003, 3, 248-252.
Hiob et al. Elastomers in Vascular Tissue Engineering. Curr. Opin. Biotechnol. 2016, 40, 149-154.
Jamshidian et al. Poly-Lactic Acid: Production, Applications, Nanocomposites, and Release Studies. Compr. Rev. Food Sci. Food Saf. 2010, 9, 552-571.

(Continued)

Primary Examiner — Robert S Jones, Jr.
(74) Attorney, Agent, or Firm — Caesar Rivise, PC

(57) ABSTRACT

A novel polymer is provided by polymerization of xylitol and dodecanedioic acid. The polymer, poly(xylitol-dodecanedioic acid) or PXDDA, shows high elasticity. PXDDA significantly improves cell adhesion and promotes cell proliferation compared to an FDA-approved polymer, poly (lactic acid), and tissue-culture plates. PXDDA can be synthesized by a simple melt condensation polymerization without the use of any toxic catalysts.

11 Claims, 14 Drawing Sheets

(56) References Cited

OTHER PUBLICATIONS

Khonakdar et al. An Investigation of Chemical Crosslinking Effect on Properties of High-Density Polyethylene. Polymer, 2003, 44, 4301-4309.

Li et al. A Comparative Study on Poly(Xylitol Sebacate) and Poly(Glycerol Sebacate): Mechanical Properties, Biodegradation and Cytocompatibility. Biomed. Mater. Bristol Engl. 2013, 8, 1-10.

Li et al. Enzymatic and Oxidative Degradation of Poly(Polyol Sebacate). J. Biomater. Appl. 2014, 28(8), 1138-1150.

Lin et al. Diffuse Reflectance Spectroscopy for in Vivo Pediatric Brain Tumor Detection. J. Biomed. Opt. 2010, 15(6), 061709-1-061709-6.

Madhavan et al. An Overview of the Recent Developments in Polylactide (PLA) Research. Bioresour. Technol. 2010, 101, 8493-8501.

Maitz. Applications of Synthetic Polymers in Clinical Medicine. Biosurface Biotribology, 2015, 1, 161-176.

Malikmammadov et al. PCL and PCL-Based Materials in Biomedical Applications. J. Biomater. Sci. Polym. Ed. 2018, 29 (7-9), 863-893.

Migneco et al. Poly(Glycerol-Dodecanoate), a Biodegradable Polyester for Medical Devices and Tissue Engineering Scaffolds. Biomaterials, 2009, 30, 6479-6484.

Moschouris et al. The Application of Cell Sheet Engineering in the Vascularization of Tissue Regeneration. Regen. Med. 2016, 11(6), 559-570.

Natarajan et al. Polyanhydrides of Castor Oil-Sebacic Acid for Controlled Release Applications-Industrial & Engineering Chemistry Research (ACS Publications), 2014, 53, 7891-7901.

Natarajan et al. Development of Graphene Oxide-/Galactitol Polyester-Based Biodegradable Composites for Biomedical Applications ACS Omega 2017, 2, 5545-5556.

Natarajan et al. Maltitol-Based Biodegradable Polyesters with Tailored Degradation and Controlled Release for Bone Regeneration. RSC Adv. 2016, 6, 40539-40551.

Yang et al. Novel Citric Acid-Based Biodegradable Elastomers for Tissue Engineering . Adv. Mater. 2004, 16(6), 511-516.

Prucker et al. On the Glass Transition in Ultrathin Polymer Films of Different Molecular Architecture. Macromol. Chem. Phys. 1998, 199, 1435-1444.

Rai et al. Synthesis, Properties and Biomedical Applications of Poly(Glycerol Sebacate) (PGS): A Review. Prog. Polym. Sci. 2012, 37, 1051-1078.

Rezayan et al. Synthesis and Characterization of Biodegradable Semi-Interpenetrating Polymer Networks Based on Star-Shaped Copolymers of ε-Caprolactone and Lactide. Iran. J. Pharm. Res. IJPR, 2017, 16(1), 63-73.

Saini et al. Poly(Lactic Acid) Blends in Biomedical Applications. Adv. Drug Deliv. Rev. 2016, 107, 47-59.

Selvam et al. Injectable in Situ Forming Xylitol-PEG-Based Hydrogels for Cell Encapsulation and Delivery. Colloids Surf. B Biointerfaces, 2015, 126, 35-43.

Sherratt. Tissue Elasticity and the Ageing Elastic Fibre. Age, 2009, 31, 305-325.

Solorio et al. Tailoring the Physicochemical and Shape Memory Properties of the Biodegradable Polymer Poly(Glycero Dodecanoate) via Curing Conditions. J Biomed. Mater. Res. A. 2017, 105A(6), 1618-1623.

Lapidus et al. Some Factors Affecting the Release of a Water-Soluble Drug from a Compressed Hydrophilic Matrix. J. Pharm. Sci. 1966, 55(8), 840-843.

Pitt et al. Sustained Drug Delivery Systems II: Factors Affecting Release Rates from Poly(epsilon-Caprolactone) and Related Biodegradable Polyesters. J. Pharm. Sci. 1979, 68(12), 1534-1538.

Tokiwa et al. Biodegradation of Synthetic Polymers Containing Ester Bonds. In Agricultural and Synthetic Polymers; ACS Symposium Series; American Chemical Society, 1990, 136-148.

Tran et al. Biodegradable Elastomeric Polymers and MEMS in Tissue Engineering. In Biomaterials for MEMS; Chiao, J.-C., Ed.; Pan Stanford Publishing, 2011, 1-32.

Ur-Rehman et al. Xylitol: A Reviewon Bioproduction, Application, Health Benefits, and Related Safety Issues. Crit. Rev. Food Sci. Nutr. 2015, 55, 1514-1528.

Wang et al. A Tough Biodegradable Elastomer. Nat. Biotechnol. 2002, 20, 602-606.

Wong et al. A novel poly(xylitol-co-dodecanedioate)/hydroxyapatite composite with shape-memory behaviour. Materials Letters, 2014, 126, 105-108.

Wu et al. High Molecular Weight Poly(Butylene Succinate-Co-Butylene Furandicarboxylate) Copolyesters: From Catalyzed Polycondensation Reaction to Thermomechanical Properties Biomacromolecules 2012, 13, 2973-2981.

Zhang et al. UV-Excitable Fluorescent Poly(Lactic Acid) Fibers. Polym. Eng. Sci. 2016, 373-379.

Bhatia et al. The role of optical spectroscopy in epilepsy surgery in children, Neurosurg Focus, 2008, 25(3), 1-8.

Engineer et al. Review on Hydrolytic Degradation Behavior of Biodegradable Polymers from Controlled Drug Delivery System. Trends in Biomaterials & Artificial Organs, 2011, 25(2), 79-85.

Hirose et al. Glass transition and thermal decomposition of epoxy resins from the carboxylic acid system consisting of ester-carboxylic acid derivatives of alcoholysis lignin and ethylene glycol with various dicarboxylic acids. Thermochimica Acta 431, 2005, 76-80.

Kolanthai et al. Copolyesters from Soybean Oil for Use as Resorbable Biomaterials. ACS Sustain. Chem. & Eng. 2015, 3, 880-891.

Li et al. Engineering Hydrolytic Degradation Behavior of Poly(Lactic-co-Glycolic Acid) through Precise Control of Monomer Sequence. In Sequence-Controlled Polymers: Synthesis, Self-Assembly, and Properties; ACS Symposium Series; American Chemical Society, 2014, 271-286.

* cited by examiner

Fig. 8A　　　　　Fig. 8B　　　　　Fig. 8C
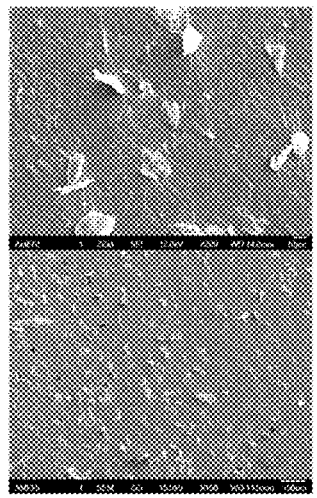 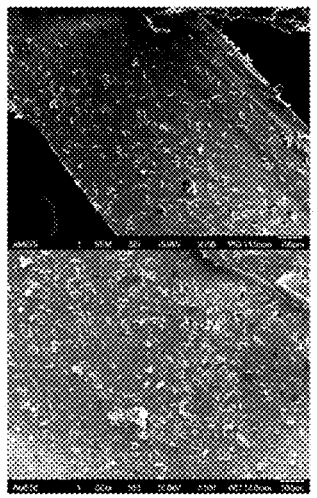 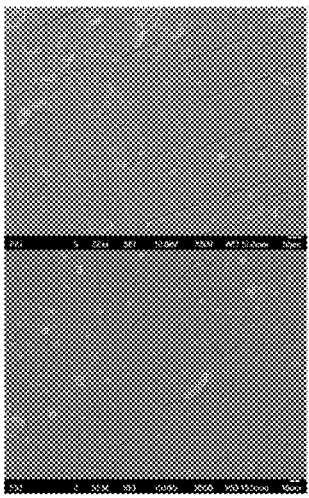
Fig. 8D　　　　　Fig. 8E　　　　　Fig. 8F
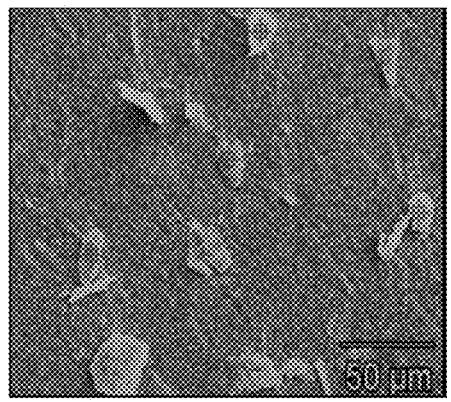
Fig. 8G
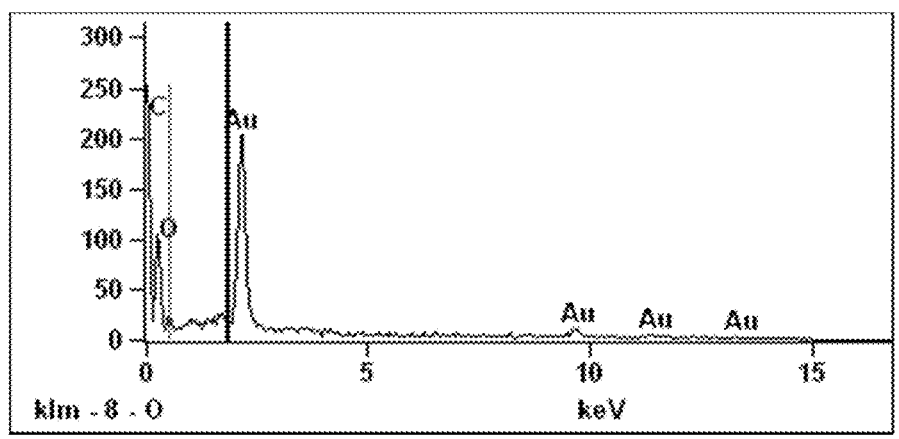
Fig. 8H

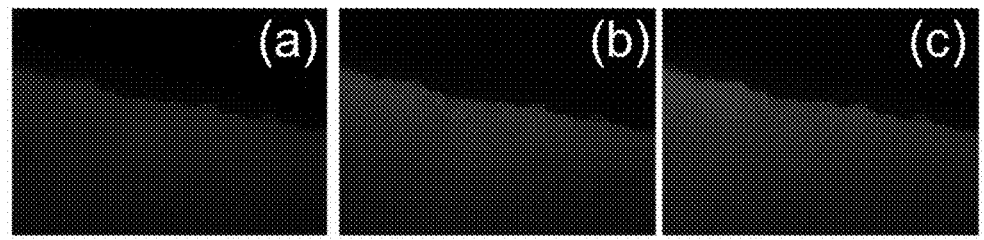
Fig. 9A     Fig. 9B     Fig. 9C
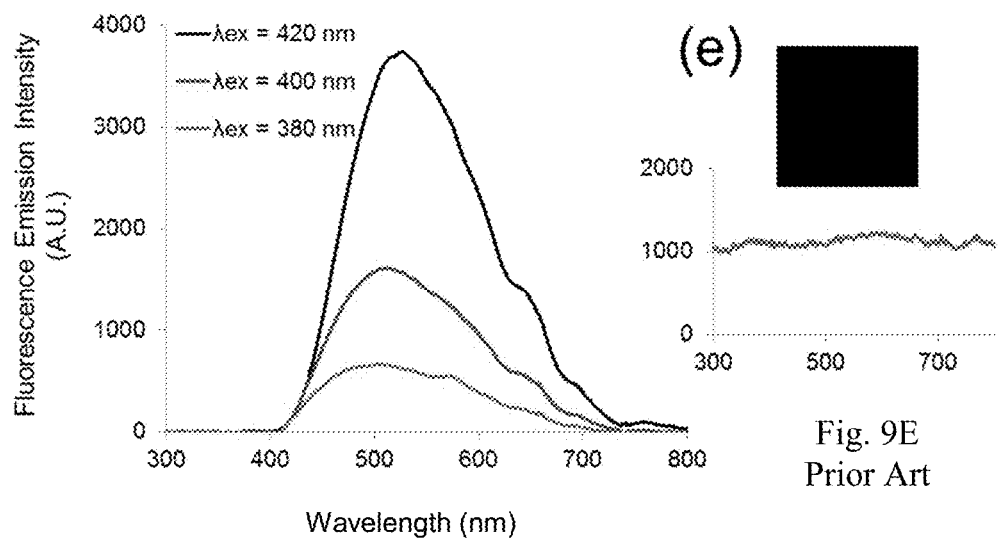
Fig. 9D
Fig. 9E
Prior Art

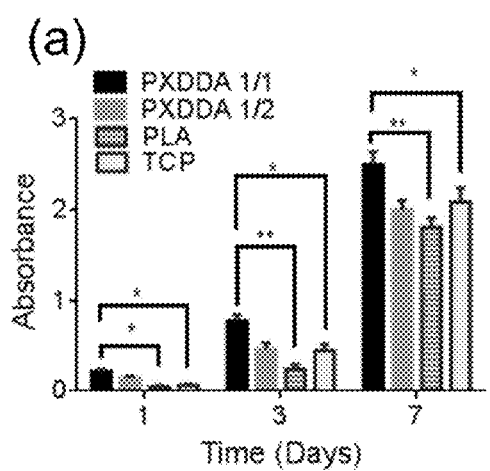
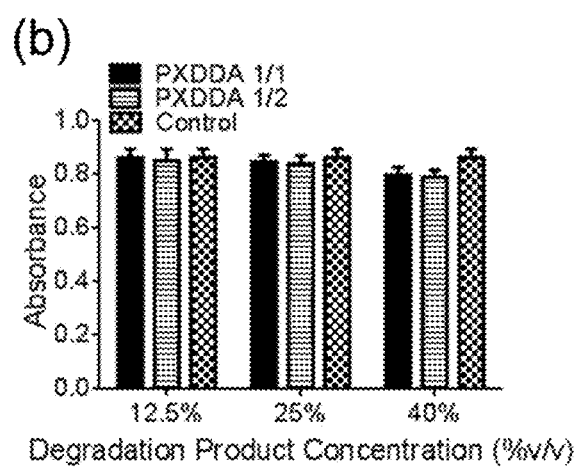
Fig. 10A  Fig. 10B
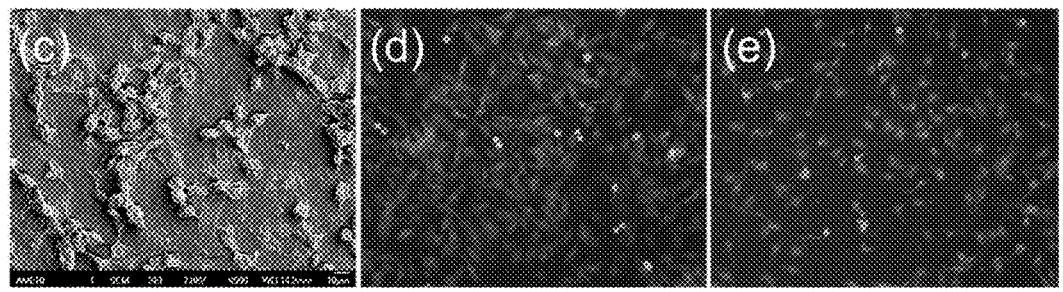
Fig. 10C  Fig. 10D  Fig. 10E Fig. 11A
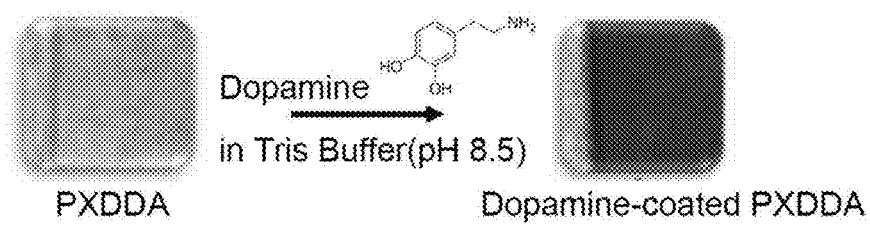
Fig. 11B
Fig. 11C
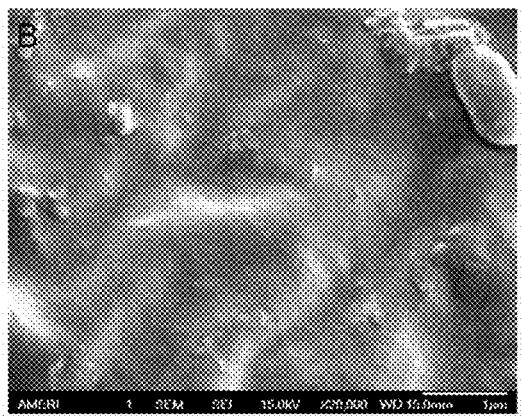
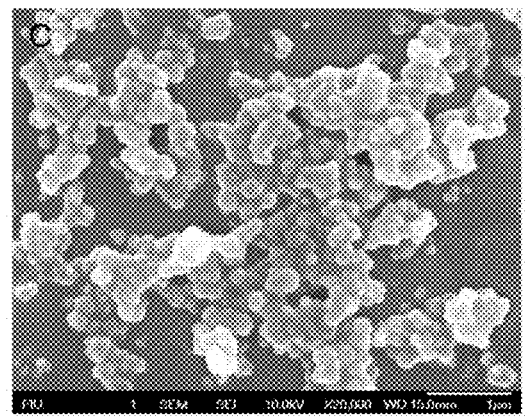
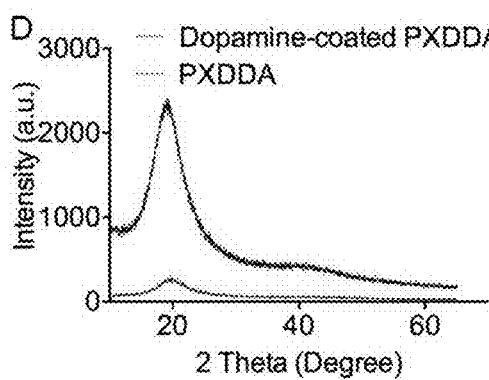
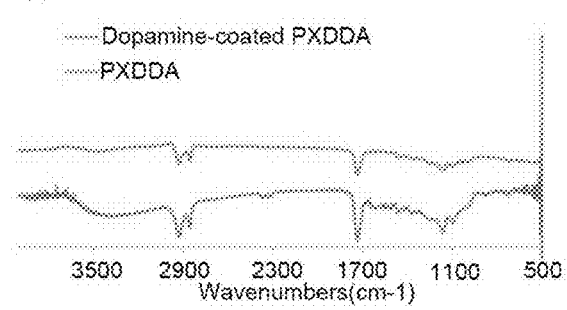
Fig. 11D
Fig. 11E FIG 16.C  Fig. 16D

GROWTH FACTOR-LOADED ELASTIC POLY(XYLITOL-DODECANEDIOIC ACID) POLYMER FOR TISSUE ENGINEERING

BACKGROUND OF THE INVENTION

1. Field of Invention

This invention relates to polymers and polymer synthesis, and particularly to highly elastic polymers suitable for use in tissue engineering applications.

2. Description of Related Art

The purpose of tissue engineering is to repair damaged tissues with the support of biomaterials (semi-synthetic, synthetic, or natural) (1). Up to now, different kind of biomaterials, such as metals, ceramics, composites, natural and synthetic polymers, have been widely studied for tissue engineering applications (1-3). Among these different groups of biomaterials, synthetic polymers are preferred for many applications in soft tissue regeneration because of their adjustable degradation rate and mechanical properties to soft tissues by different chemical functionalization and processing routes (4-6). The regeneration of soft tissues, such as lung, intestine, muscle, and skin, requires a soft biomaterial that can withstand various deformations without causing mechanical stress in surrounding tissues (7).

Polyester is one kind of these polymer biomaterials that has many applications in tissue engineering due to its biocompatibility and biodegradability (8). Most polyester polymers degrade without any dramatic structural changes during the hydrolytic degradation because of surface and bulk erosion mechanisms (7, 9-11). Poly(lactic acid) (PLA), poly(caprolactone) (PCL), poly(lactic-co-glycolic acid) (PLGA) are examples of polyesters, which have been approved by the FDA and widely used in different biomedical fields like tissue engineering and drug delivery (9,12). However, their applications in soft tissue regeneration are limited by their high stiffness and low elasticity that do not mimic the extracellular matrix (ECM) of soft tissues (13-15). The synthesis routes for these polyester polymers also have several disadvantages, such as complex and costly procedures, toxic catalysts or a large amount of organic solvents required, and nonrenewable resources. These significant drawbacks have led researchers to synthesize new polyester materials with higher elasticity and adjustable mechanical properties to meet the specific needs for soft tissue applications such as tendons, heart valves, skin, wound dressing, nerves and blood vessels (8,16,17). Additionally, using renewable resources for the synthesis of a polyester polymer at a low cost will bring new potential for biomedical applications (18-20).

Accordingly, it is desired to provide improved polymers that are sufficiently soft and elastic for use in soft tissue regeneration and are synthesized from biocompatible monomers with a simple and inexpensive synthetic route, without using any toxic solvents or excess amount of catalysts.

It is further desired to provide new elastic polymers that are biocompatible and biodegradable, which are suitable for use in medical and non-medical applications. It is still further desired to provide such polymers with tunable properties.

All references cited herein are incorporated herein by reference in their entireties.

BRIEF SUMMARY OF THE INVENTION

A first aspect of the invention is a polymer comprising xylitol and dodecanedioic acid.

In certain embodiments, the polymer is a poly(xylitol-dodecanedioic acid) (PXDDA) represented by the following general formula:

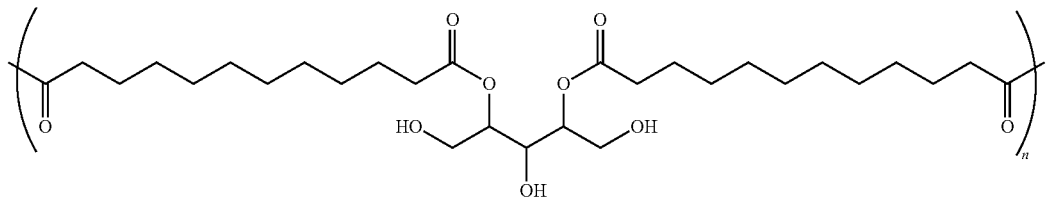

where n is greater than 1.

In certain embodiments of the polymer, a molar ratio of xylitol to dodecanedioic acid in the polymer is from 0.5 to less than 2.

In certain embodiments, the polymer is elastomeric, has an average tensile Young's modulus of $0.1\pm10.034$ MPa, an average elongation at rupture of $66\%\pm17\%$, and an ultimate tensile strength of $0.065\pm0.03$ MPa.

In certain embodiments, the polymer has an average Young's modulus of $0.69\pm0.08$ MPa, an average elongation at rupture of $27\%\pm8.1\%$ and an ultimate tensile strength of $0.165\pm0.04$ MPa.

In certain embodiments, the polymer is fluorescent.

A second aspect of the invention is a method for synthesizing a poly(xylitol-dodecanedioic acid), said method comprising polymerizing xylitol and dodecanedioic acid to form the poly(xylitol-dodecanedioic acid).

In certain embodiments of the method, the polymerizing comprises melt condensation.

In certain embodiments of the method, the xylitol and the dodecanedioic acid are combined in a molar ratio of xylitol to dodecanedioic acid from 0.5 to less than 2.

In certain embodiments of the method, the polymerizing comprises adding 0.01 wt. % to 2 wt. % of sulfuric acid to a mixture of xylitol and dodecanedioic acid to accelerate a polymerization reaction.

A third aspect of the invention is a composition comprising the polymer of the invention and at least one growth factor bonded to the polymer.

In certain embodiments, the polymer is coated with polydopamine and the growth factor is bonded to the polydopamine.

In certain embodiments, the growth factor is fibroblast growth factor.

BRIEF DESCRIPTION OF SEVERAL VIEWS OF THE DRAWINGS

The invention will be described in conjunction with the following drawings, wherein:

FIG. 8A is an SEM micrograph of a surface of a PXDDA polymer (1/1).

FIG. 8B is an SEM micrograph of a cross-section of a PXDDA polymer (1/1).

FIG. 8C is an SEM micrograph of a surface of a PXDDA polymer (1/1) after eight weeks of hydrolytic degradation.

FIG. 8D is an SEM micrograph of a surface of a PXDDA polymer (1/2).

FIG. 8E is an SEM micrograph of a cross-section of a PXDDA polymer (1/2).

FIG. 8F is an SEM micrograph of a surface of a PXDDA polymer (1/2) after eight weeks of hydrolytic degradation.

FIG. 8G is a magnified SEM micrograph of a surface of a PXDDA polymer, wherein certain dots were labeled for the detection of EDS spectrum.

FIG. 8H shows an EDS spectrum of a PXDDA 1/1 surface.

FIGS. 9A, 9B and 9C are photographs showing the fluorescent emission of blue, green and red light by PXDDA films, wherein the dark area in each image is a glass slide.

FIG. 9D shows fluorescence emission spectra of fluorescent PXDDA 1/1.

FIG. 9E is a fluorescent spectrum showing the absence of auto-fluorescence in poly(lactic acid) (PLA).

FIG. 10A shows an MTT assay.

FIG. 10B shows the cytotoxicity of cross-linked PXDDA polymers' 8-week degradation products at three different concentrations as evaluated by MTT assay after 36 hours. Data in FIGS. 10A and 10B are indicated as means±SE with n=3 samples/group.

FIG. 10C is an SEM micrograph of HUVEC cells seeded on a PXDDA polymer.

FIG. 10D is a photograph by a fluorescent microscope at 10× magnification showing the morphologies of GFP-tagged HUVEC cells cultured on a tissue culture plate.

FIG. 10E is a photograph by a fluorescent microscope at 10× magnification showing the morphologies of GFP-tagged HUVEC cells cultured on PLA.

FIG. 11A shows the dopamine coating procedure schematically.

FIG. 11B is an SEM micrograph of non-coated PXDDA.

FIG. 11C is an SEM micrograph of PXDDA coated with polydopamine.

FIG. 11D shows XRD spectra of PXDDA before and after polydopamine coating.

FIG. 11E shows FTIR spectra of polydopamine-coated PXDDA polymer.

FIG. 16C is an SEM micrograph of fibroblast cells on FGF-polydopamine-coated PXDDA.

FIG. 16D is an SEM micrograph of fibroblast cells on FGF-polydopamine-coated PXDDA.

Figure 1A:
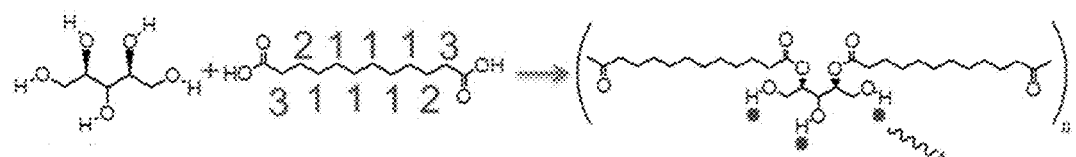
FIG. 1A shows a reaction scheme for the synthesis of poly(xylitol-co-dodecanedioic acid) (Red dots indicate that these —OH groups might also be involved in esterification because it is a random polymerization).

The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS OF THE INVENTION

Compositions of the Invention

The invention comprises prepolymers and polymers based on xylitol and dodecanedioic acid monomers, as well as composites containing such polymers. The poly(xylitol-dodecanedioic acid) polymers can be represented by the following general formula:

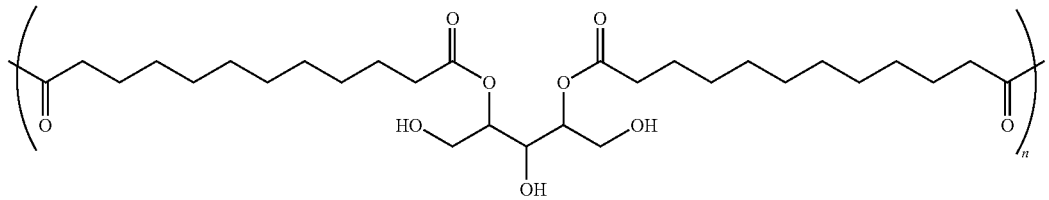

where n is greater than 1. In certain embodiments, n is from 2 to 10000 or more. For example, in certain embodiments, the value of n is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000 or 10000, or is limited to a range defined by any two of said values.

Xylitol is a polyol with multiple hydroxyl groups and belongs to a renewable resource. It is a sugar alcohol, which can be extracted from vegetables, fruits, corn fibers, and birch wood. The flavor of xylitol is like that of sugar (i.e., sucrose), but with 40% less calories than sugar. It does not increase the blood sugar levels as sugar does (21). This property can increase the use of xylitol for diabetics and those with blood sugar related problems. Xylitol is cheap, abundant, nontoxic, and approved by the FDA. It also has many other good properties, such as healing, anti-bacterial, and anti-cariogenic properties, pharmacokinetics, and biocompatibility, as well as promoting bone metabolism (4,22-25). However, xylitol is a powder and soluble in water. It cannot support cell growth as a block of a scaffold for tissue regeneration.

To address this problem, a nontoxic cross-linker, dodecanedioic acid, is used to polymerize xylitol into a polymer. Dodecanedioic acid is a biocompatible dicarboxylic acid which enables more crosslinking sites for a network formation. Dodecanedioic acid helps to maintain normal blood sugar and energy levels without increasing the blood glucose load and it does not cause any environmental effects or considerable adverse effects on human health. It also has attractive biological properties, making it useful as a nutrient, a membrane stabilizer, an energy source, and for storage (23,26,27).

The regenerative ability of the new polymer can be enhanced by the grafting of growth factors. Non-limiting examples of growth factors include but are not limited to fibroblast growth factor (FGF), epidermal growth factor (EGF), cilliary neurotrophic factor (CNTF), nerve growth factor (NGF), platelet-derived growth factor (PDGF), vascular endothelial growth factor (VEGF), hepatocyte growth factor (HGF), heparin-binding EGF-like growth factor or HB-EGF and transforming growth factor-alpha. FGF is a preferred growth factor and was used to prove the concept. FGF is a critical growth factor that is representative of the types of GF's associated with the repair and regeneration of tissues. FGF has growth factor receptors (FGFRs), and the main signaling through the stimulation of FGFRs is the RAS/MAP kinase pathway. With their potential biological functions, FGFs have been utilized for the regeneration of damaged tissues, including skin, blood vessel, muscle, adipose, tendon/ligament, cartilage, bone, tooth, and nerve initially been identified as a protein capable of promoting fibroblast proliferation and is now known to comprise 22 members. FGFs exert multiple functions through the binding into and activation of fibroblast.

To bind growth factors onto the polymer material, many methods have been developed. A dopamine coating method is an effective way to bind growth factors. Dopamine mainly tethered GFs onto substrates through the covalent bonding between the amino groups of GFs and the quinone groups (the catechol groups in dopamine can be oxidized into quinone groups) of polydopamine via Michael-type addition reactions and Schiff-base reactions.

The structure and properties of the polymer can be modified by adjusting the molar ratio of xylitol and dodecanedioic acid combined in the polymerization reaction. The molar ratio of xylitol to dodecanedioic acid in the polymer is preferably from 0.1 to 10, and more preferably from 0.5 to less than 2. Particularly preferred embodiments have a molar ratio of 0.5 or 1 (i.e., 1:2 or 1:1 xylitol to dodecanedioic acid).

The physicochemical and biological properties of the new PXDDA polymer were characterized. Fourier transform infrared (FTIR) confirmed the formation of ester bonding in the polymer structure, and thermal analysis demonstrated that the polymer was completely amorphous. The polymer shows high elasticity. Increasing the molar ratio of dodecanedioic acid resulted in higher hydrophobicity and lower glass transition temperature. Further, the polymer degradation and in vitro dye release studies revealed that the degradation and dye release from the polymer became slower when the amount of dodecanedioic acid in the composite increased. Biocompatibility studies showed that both the polymeric materials and the degraded products from the polymer did not show any toxicity. Interestingly, the PXDDA polymer significantly improved the cell adhesion and promoted cell proliferation compared to a widely-used polymer, poly(lactic acid), and tissue-culture plates. Overall, these results confirm that a new, elastic, biodegradable polymer with auto-fluorescent properties has been successfully synthesized and also has promising potential for biomedical applications in drug delivery and tissue engineering.

Polymers of the invention preferably exhibit the properties listed in Table 1 below.

TABLE 1

Mechanical Properties of PXDDA

| Property | Preferred | Narrower Range 1 |
| --- | --- | --- |
| Young's Modulus | 0.01-1 MPa | 0.1-0.8 MPa |
| Average Elongation at Rupture | 10-100% | 15-95% |
| Ultimate Tensile Strength | 0.01-0.25 MPa | 0.05-0.20 MPa |

In a particularly preferred embodiment, the polymer has an average tensile Young's modulus of 0.11±0.034 MPa, an average elongation at rupture of 66%±17%, and an ultimate tensile strength of 0.065±0.03 MPa.

In another particular preferred embodiment, the polymer has an average Young's modulus of 0.69±0.08 MPa, an average elongation at rupture of 27%±8.1% and an ultimate tensile strength of 0.165±0.04 MPa.

Polymers of the invention are preferably elastomeric.

Polymers of the invention are preferably autofluorescent (i.e., are fluorescent without the need for additional fluorophores). The polymers can emit light in the blue (400-500 nm), green (500-550 nm) and/or red (550-650 nm) wavelength(s). The autofluorescence of the polymer is attributed to double bonds and hydroxyl functional groups in the polymer molecular structure.

The physical state of the inventive polymers is not particularly limited. The polymer can be provided in liquid, solid or semi-solid form. The polymer can be, e.g., injection molded, cast, thermoformed or injection-molded to form objects such as, e.g., sheets, foams, matrices and other three-dimensional objects.

The inventive polymer can be provided alone or in combination with additional materials in composites. The additional materials include but are not limited to active pharmaceutical ingredients, ceramic structural reinforcement materials, etc.

The unique combination of properties possessed by the polymer of the invention make it suitable for use in a wide variety of applications. The inventive polymer is particularly well suited for use in tissue regeneration, such as for repairing or replacing intervertebral discs, bone, and cartilage (4,51-53).

Polymer Synthesis

The polymer of the invention is provided by polymerization of xylitol and dodecanedioic acid. In the most preferred embodiment, the polymerization proceeds by a melt condensation synthesis, which is a low cost and simple method without the addition of any toxic catalyst. The polymers can be synthesized with different stoichiometric ratios of xylitol and dodecanedioic acid. The properties of the polymers can be modified by modifying the molar ratios of the xylitol and dodecanedioic acid and/or by modifying the curing time. Preferred molar ratios are discussed above.

The synthesized polymer was made into a thin film and then coated by dopamine. The dopamine-coated polymer film was grafted with FGF. In vitro released profile of FGF was investigated and the effect of FGF-loaded polymer on cell viability was studied.

The invention will be illustrated in more detail with reference to the following Examples, but it should be understood that the present invention is not deemed to be limited thereto.

EXAMPLES

1. Materials and Methods 1.1. Materials

Xylitol and dodecanedioic acid were obtained from Alfa Aesar. Dimethyl sulfoxide (DMSO) and 3-(4,5Dimethylthiazol-2-yl)-2,5-diphenyl tetrazolium bromide (MTT) were obtained from Sigma. All other commercially available solvents were purchased from Fisher Scientific company. All chemicals were used as received and they were of analytical grade.

1.2. Synthesis of poly(xylitol-co-dodecanedioic acid)

A pre-polymer of poly(xylitol-co-dodecanedioic) (PXDDA) was first synthesized by simultaneously melting of a 2/1, 1/1, and 1/2 molar ratios of xylitol and dodecanedioic acid at 165° C. in a 250 mL reaction flask purged with nitrogen gas at a flow rate of ~120 $cm^3$ $min^{-1}$. Several microliters of sulfuric acid were added and the reaction was maintained for 2 h at 155° C., thus a pre-polymer was obtained. To purify the prepolymer, ethanol (at a ratio of PXDDA/ethanol: 1/2) was added into the pre-polymer and then the PXDDA/ethanol solution was precipitated in the water (at a ratio of PXDDA solution/water: 1/3), followed by lyophilization for two days. After that, the pre-polymer was again dissolved in ethanol and cast onto aluminum molds for curing. The cast pre-polymers were then kept at 120° C. under vacuum (-700 mmHg) for 3 days, followed by cooling down to the room temperature. In the end, PXDDA discs approximately 3 mm in thickness (radius=7.5 mm) were peeled off the molds and distilled water was added to remove unreacted monomers and purify the polymer.

1.3 Characterization of Synthesized PXDDA

The synthesized polymer is insoluble in common solvents after the curing process, whiles the pre-polymer has the ability to dissolve in many different solvents such as ethanol, chloroform, tetrahydrofuran (THF), dimethylformamide (DMF), and dichloromethane (DCM). Therefore, the pre-polymer was used in the NMR spectrum and all the other tests were carried out on the cured polymer. It is worth mentioning that the pre-polymer molecular weight was not measured as it would not reveal the molecular weight of the ultimately crosslinked polymer.

The chemical structure of PXDDA was analyzed by proton nuclear magnetic resonance ($^1$H NMR), Fourier transform infrared (FTIR), and x-ray diffraction (XRD). $^1$H NMR was recorded on a Mercuryplus spectrometer (400 MHz) with $CDCl_3$ as a solvent at 25° C. FTIR was performed on a Jasco FT/IR-4100 apparatus over the region 4000-400 $cm^{-1}$. XRD analysis was measured using a Siemens D5000 X-Ray Diffractometer with monochromatic CuKα radiation, 40 kV accelerating voltage, a current of 30 mA, and scanning in the 2 θ range of 10° to 65° with a step size of 0.05 at 27° C. The thermal properties of the PXDDA were determined over the temperature range of 25 to 800° C. at a 10 $K\text{-}min^{-1}$ heating rate with SDT-Q600 (Simultaneous Thermogravimetric analyzer and Differential Scanning Calorimeter).

1.4. Mechanical Properties

The tensile test was carried out on sample strips (30×9×1.5 mm, length×width×thickness) using an MTI SEMtester (SEM/LM-based Tensile Systems, Albany, USA), at room temperature with a cross-head speed of 1 mm $min^{-1}$, and a 100-N load cell. The Young's modulus (E), ultimate tensile strength (UTS), and percent elongation were determined. A Durometer Shore A scale was used to study the resistance of the PXDDA towards indentation and its rigidity against moderate stress. A macro hardness test was performed according to ASTM D2240. All were measured on six specimens at room temperature and the average is reported.

1.5 Contact Angle Measurements

Biolin Scientific contact angle optical tensiometer (Theta Lite, Espoo, Finland) was used to study the water-in-air contact angle of the cured polymers at room temperature. An ultrapure water droplet of 1 μl volume was placed on the surface of PXDDA films fixed on the glass slides. All measurements were performed after equilibrium was reached. The data are reported as a mean±standard deviation (SD) for six independent readings.

1.6 Swelling of PXDDA

To study the water molecules' diffusion rate in the polymeric network, the cured PXDDA discs (radius=3 mm) were placed in 50 ml distilled water, ethanol, DCM, and DMF at 37° C. The swollen discs were removed from the water and solvents at different time points. Excess surface water and solvents were absorbed on a filter paper and the discs were weighed (Ws). The discs were then kept in a vacuum oven at 37° C. for 5 days to get constant weight (Wd). The percentage of swelling was determined by the following formula: % swelling=[(Ws−Wd)/Wd]×100.

1.7 Dye Release Kinetics

To consider the polymer potential for drug release applications, the release of a hydrophobic dye (Rhodamine B base; RBB) and a hydrophilic dye (Rhodamine B; RB) were studied. The prepolymer (95 wt %) and the dye (5 wt %) were dissolved in 3 ml DMF, followed by stirring to get a homogenous solution. After solvent evaporation at room temperature for 3 days, the polymeric discs (4×4×1 mm) were cured in the vacuum oven similar to the previous samples. The discs were put in 10 ml of PBS with a neutral pH at 37° C. on a shaker. At the end of the designated time points, 50 μL of the solution was collected and 50 μL of fresh PBS was added to the releasing tube. Finally, the dye absorption was measured at 553 nm using a spectrophotometer (Spectramax Gemini EM). The measurements were carried out in triplicate. The dye concentration was determined with the calibration curves. Finally, a cumulative release profile was analyzed.

1.8 In Vitro Degradation Behavior of PXDDA

The degradation behavior of PXDDA discs (n=3) was studied by weight loss and FTIR spectroscopy after exposure to the aqueous solution (Gibco buffered saline solution, pH 7.4) at 37° C. over a 12-week period. Polymeric discs were taken weekly, dried at 40° C. and then weighed again.

1.9 Auto-Fluorescence Property of PXDDA

The fluorescence property of the PXDDA polymer was studied experimentally at room temperature. Fluorescence emission spectra were conducted using a QEA0303 fluorescence spectrophotometer (Spectra-Physics, Mountain View, Calif.) on sample strips (4×1×1 cm) with an integration time of 5 seconds. The spectra of excitation were measured at three different excitation wavelengths; $\lambda$ex=380 nm, 400 nm, and 420 nm. At the same time, the PXDDA sample was scanned by using the fluorescence microscope (Nikon Eclipse TE2000-S).

1.10 Biocompatibility of PXDDA Discs

The ability of polymeric discs for supporting cells adhesion and growth was evaluated by MTT (3-[4,5-dimethyl-thiazol-2-yl]-2,5 diphenyltetrazolium bromide) and scanning electron microscopy (SEM) (JEOL JSM-6330F; Tokyo, Japan). Human umbilical vein endothelial cells (HUVECs) were grown in endothelial growth medium (EGM-2, Lonza) supplemented with 10% fetal bovine serum (Gibco) and 1% PSG (Penicillin-Streptomycin-Glutamine, Gibco). The polymeric discs were sterilized under UV light source for 2 h, immersed in ethanol for 30 min and then rinsed in phosphate buffered saline (PBS). After washing the discs completely with PBS, they were kept in EGM-2 medium for 24 h before culturing the cells. The polymeric discs were placed in a 24-well plate and they can completely cover the surface of the wells. Cells were then seeded on the surface of the polymeric discs. PLA (material control) and tissue culture plate (TCP) served as controls. HUVECs with a density of $8\times10^3$ cells/well were seeded and then cultured for 1, 3, and 7 days. At each specific time, the HUVEC cells' viability and proliferation was evaluated by MTT assay (0.5 mg/ml). The reduced crystal formazan was dissolved in DMSO and the absorption of DMSO was measured at 570 nm using a spectrophotometer (SpectraMax® 190 Microplate Reader). At the same time, the cellular toxicity of degradation product of PXDDA on HUVEC cells was also evaluated. For this purpose, 104 cells were first seeded and cultured on the 96-well plates for 3 days. The degradation products were diluted with culture medium to obtain different concentrations (12.5, 25, and 40% v/v), and they were then added into the cells. After 36 h, 20 µl of MTT solution was added and the plated was incubated at 37° C. for 4 h. After adding 200 µl of DMSO, the absorbance was recorded at 570 nm. The measurements were carried out in triplicate.

The morphology of cultured cells on a polymeric disc was also observed by SEM. After a day of culture, the cells were fixed by 2.5% glutaraldehyde solution for 2 h, dehydrated through a series of graded ethanol (25, 50, 70, 90, 95, 100%), and coated by gold. The samples were observed on a SEM (JEOL JSM-6330F Electron Microscope).

1.11 Preparation of (Dopamine-HCL)-Coated PXDDA Discs

A dopamine solution was prepared by dissolving 4 mg of dopamine in each ml of 10 mM Tris-HCl buffer solution (pH 8.5). For coating, PXDDA discs were immediately immersed into a dopamine hydrochloride solution at 37° C., and the solution was gently shaken up to 24 h at 100 rpm. At each time point, PXDDA discs were completely washed in deionized water for 1 h to remove the extra amount of dopamine which did not react. The coated PXDDA discs were then dried in the oven for 24 h at 40° C.

The polydopamine-coated PXDDA samples were characterized by Fourier-transform infrared spectroscopy (FTIR; Jasco FT/IR-4100) and X-ray powder diffraction (XRD; Siemens D5000 X-ray Diffractometer with monochromatic Cu K$\alpha$ radiation, a 40 kV accelerating voltage, a current of 30 mA, and scanning in the 2$\theta$ range of 10° to 60° with a step size of 0.05) to confirm the dopamine layers deposition. Dopamine on PXDDA discs were also quantified using the BCA assay. The coated discs of 8 mm diameter were treated with 300 µL BCA working reagent and incubated at 37° C. for 120 min. For detecting the concentration of BCA, we used a spectrometer to determine the absorbance at 562 nm (SpectraMax 190 Microplate Reader).

1.12 Immobilization and Release of Fibroblast Growth Factor

Polydopamine-coated PXDDA discs were immersed in 800 µL of Fibroblast Growth Factor (FGF) solutions prepared by dissolving different amounts of FGF (250 and 500 ng) in a 10 mM Tris-HCl buffer (1 ml, pH 8.5) and incubated at 37° C. for around 24 h with gentle shaking. The discs then were rinsed with water twice. An immobilized amount of FGF was detected using enzyme-linked immunosorbent assay (ELISA). The final immobilized FGF was measured by subtracting the amount of FGF in the supernatant of the Tris-HCl buffer solution from the initial amount in the original solution.

The release kinetics of FGF from the discs were also studied in the PBS with the ELISA kit. PXDDA discs were immersed in the 1.5 ml of PBS solution and placed on a shaker at 37° C. At each interval, 500 µL of the supernatants release medium was collected and freshened with an equal amount of PBS at day 3, 7, 14, 21, and 28. Supernatants from each sample were stored at −81° C. until day 28, when all samples were collected for the ELISA testing using the manufacturer's protocol. The absorbance of the samples was measured with a spectrophotometer at 450 nm with 540 nm used for correction of $\lambda$ (SpectraMax 190 Microplate Reader). All tests were performed three times.

1.13 Human Fibroblast Cells Attachment and Proliferation

Cellular behaviors on the coated PXDDA discs were studied using human fibroblast cells (ScienCell). The polydopamine-coated PXDDA discs were placed into 24-well plates. Discs were sterilized with 70% ethanol for 30 min and then washed completely with PBS. Sterilized PXDDA discs were then immobilized with Fibroblast Growth Factor by immersing in a FGF solution (500 ng/mL, 10 mM Tris-HCl buffer, pH 8.5) and then samples were incubated overnight at 37° C. Human fibroblast cells were then seeded onto the PXDDA discs at $10^5$ cells/cm$^2$ using Dulbecco's Modified Eagle Medium (DMEM, Lonza) supplemented with 10% Fetal Bovine Serum (Gibco) and 1% PSG (Penicillin-Streptomycin-Glutamine, Gibco).

Cell proliferation of fibroblast on different groups of PXDDA discs (polydopamine-coated and uncoated PXDDA and growth factor-immobilized) was determined using the 3-(4,5-dimethyl-2-thiazolyl)-2,5-diphenyl tetrazolium bromide (MTT) assay. At each time point, 80 µL of MTT solution (5 mg/mL in PBS) was added into each well, containing 720 µL of culture medium, and incubated at 37° C. for 4 h. Once completed, the medium was removed and 800 µL of DMSO were added to each well. After 10 minutes, the absorbance at 570 nm was read using a microplate reader (SpectraMax 190 Microplate Reader).

To study the effect of dopamine and fibroblast growth factor on cell attachment and spreading, the morphology of fibroblast cells cultured on different discs was observed after 3 and 7 days of culture using scanning electron microscope (SEM; JEOL JSM-6330F, Tokyo, Japan). PXDDA discs were treated with 2.5% glutaraldehyde solution in PBS for 2 h, followed by dehydration in ethanol 25-100%.

1.14 Statistical Analysis

One-way ANOVA with Tukey's post hoc test was used to compare the difference between groups. Data are shown as a mean±standard error (SE) with 3 samples in each group. The values of p<0.05 are considered statistically significant.

2 Results 2.1 Characterization of Synthesized PXDDA

Figure 1B:
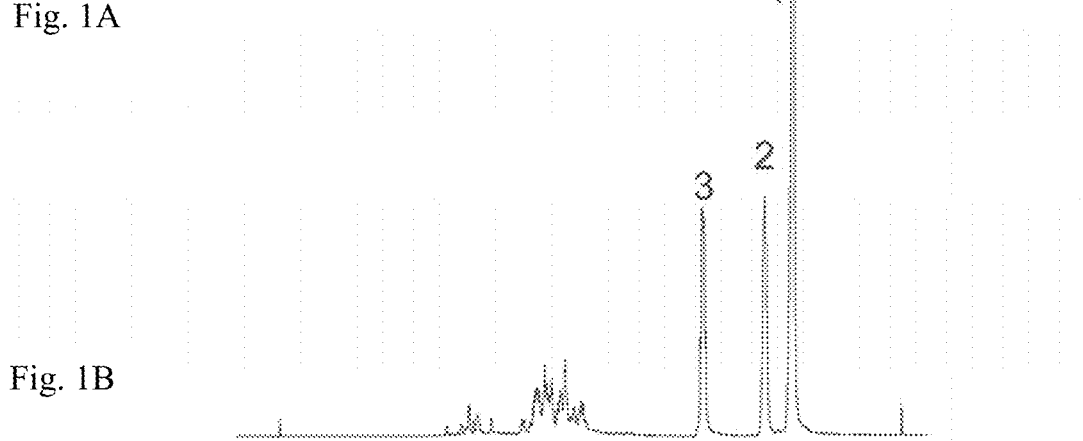
FIG. 1B is a $^1$H-NMR spectrum of PXDDA 1/1 (PXDDA wherein the molar ratio of xylitol to dodecanedioic acid is 1).
Figure 1C:
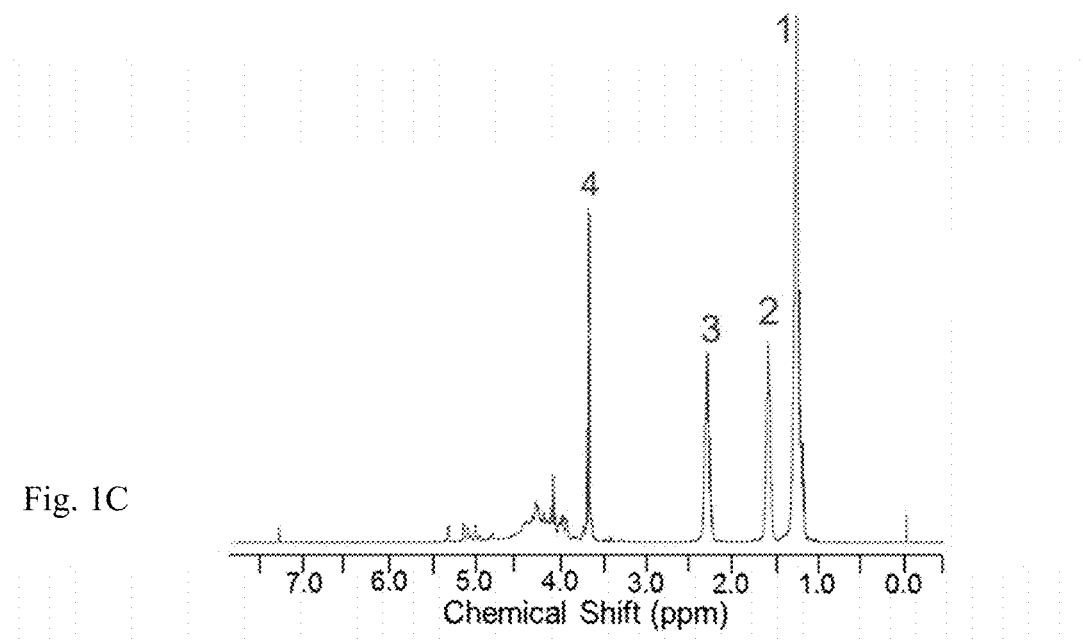
FIG. 1C is a $^1$H-NMR spectrum of PXDDA 1/2 (PXDDA wherein the molar ratio of xylitol to dodecanedioic acid is 0.5).

In this study, we synthesized xylitol-based polymers using three ratios of xylitol to DDA (2/1, 1/1, 1/2). However, we found that the polymer from the 2/1 ratio could not form a solidified shape. Therefore, only two types of PXDDA (1/1 and 1/2) polymers were fully characterized. FIG. 1A shows the structure of synthesized PXDDA. FIGS. 1B and 1C show the $^1$H NMR spectra of the pre-polymer PXDDA (1/1 and 1/2 molar ratios respectively). The peaks observed in the region of 3.6-5.3 ppm are assigned to the entire protons of xylitol. The peaks corresponding to the DDA were present between 1.2 and 2.4 ppm. The peaks between 2.2 and 2.4 ppm are ascribed to the protons located on either side of —COOH groups (HOOC—$CH_2$) (peak 3). The peak at 1.59 ppm (peak 2) belongs to the protons of the —$CH_2$ group located next to the one near the —COOH group on both sides (HOOC—$CH_2$— $CH_2$). In the end, the peak appearing around 1.25 ppm (peak 1) is attributed to the protons adjacent to the —$CH_2$ groups, which is present next to the one at 1.59 ppm (HOOC—$CH_2$—$CH_2$— $CH_2$—$CH_2$). In the PXDDA 1/2 structure (FIG. 1C), the peak appearing around 3.66 ppm (peak 4) is attributed to the extra branches which are formed because of the excess amount of DDA monomer.

Figure 2:
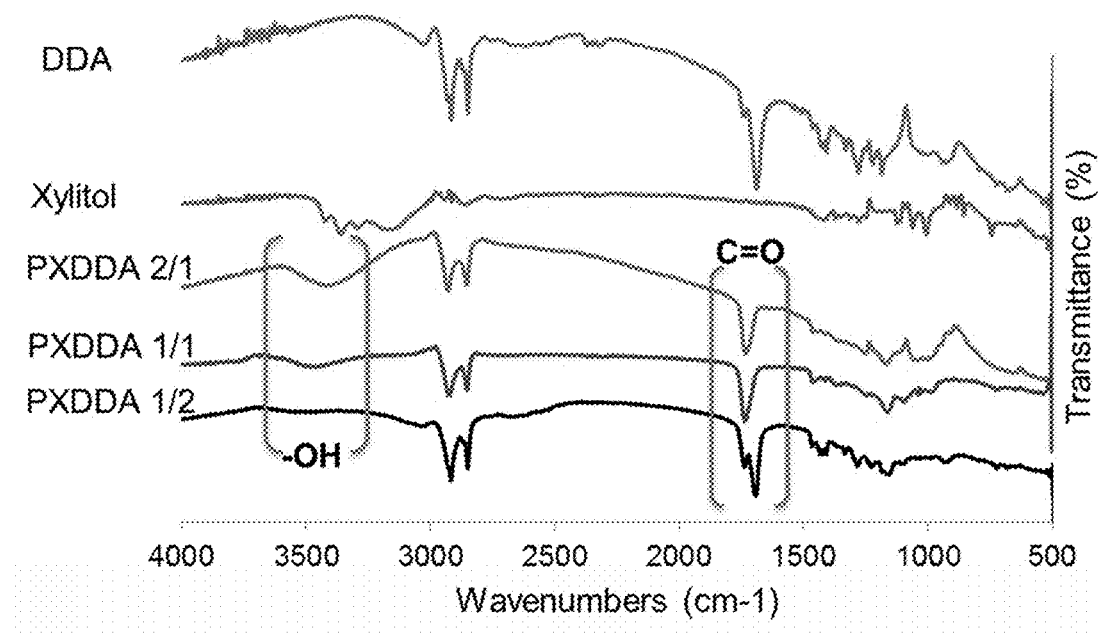
FIG. 2 shows FTIR spectra of xylitol, dodecanedioic acid (DDA), and PXDDA polymers (2/1, 1/1, 1/2).

As reported by FTIR spectrum of PXDDA in FIG. 2, the sharp peak located at 1735 $cm^{-1}$ is due to the C=O stretch, which is a characteristic peak for ester linkages. The peak detected at approximately 1120.43 $cm^{-1}$ is assigned to the C—O group of xylitol. The broad peak presented at 3378.67 $cm^{-1}$ corresponds to vibration bands of the hydrogen-bonded hydroxyl groups of xylitol. PXDDA 1/2, however, shows a shoulder next to 1730 $cm^{-1}$, demonstrating a higher extent of esterification.

Figure 3A:
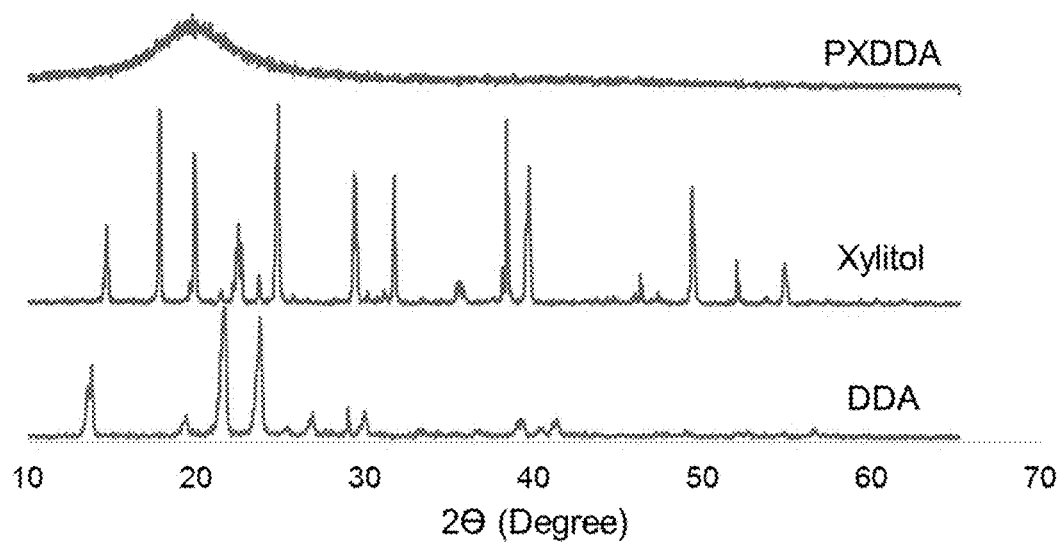
FIG. 3A shows XRD spectra of Xylitol, DDA, and PXDDA.

The XRD patterns of monomers and PXDDA polymer (1/1 as a representative) are shown in FIG. 3A. It is clearly shown that almost all the peaks in xylitol and DDA disappeared. Only a steamed-bun-like peak in the range of 15-25° was observed, which suggested that PXDDA polymer is more amorphous than crystalline.

Figure 3B:
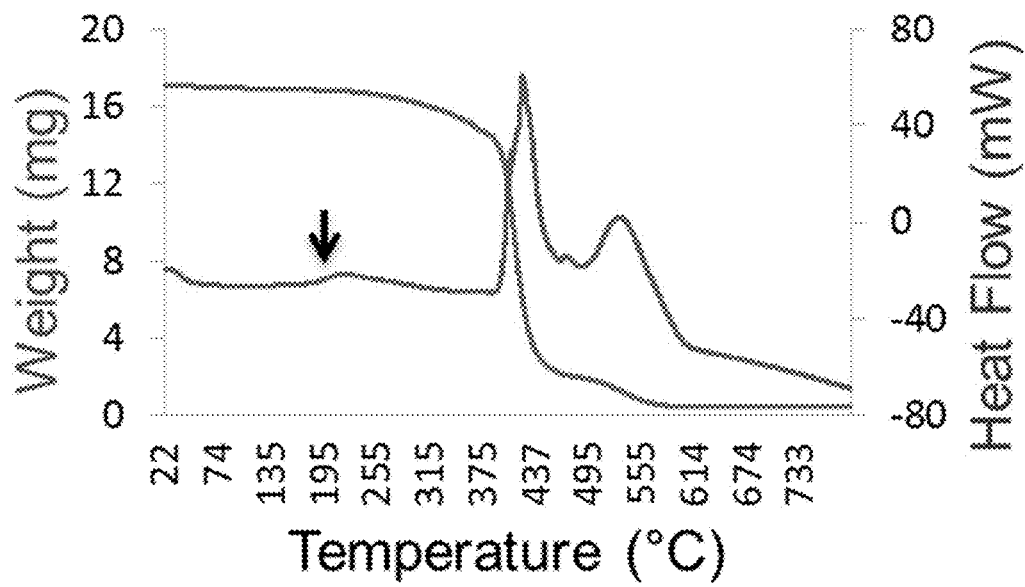
FIG. 3B shows TGA-DSC curves of PXDDA 1/1.
Figure 3C:
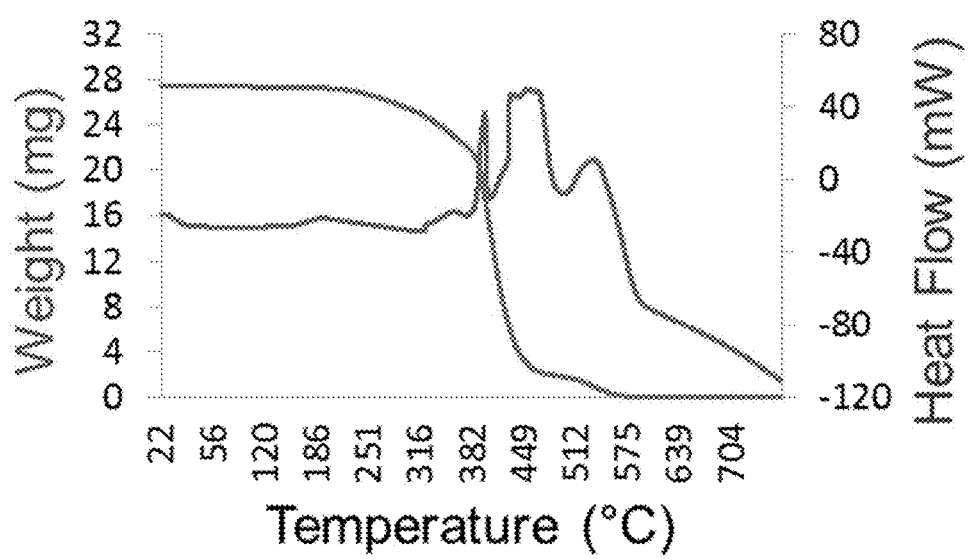
FIG. 3C shows TGA-DSC curves of PXDDA 1/2.

TGA-DSC analysis was performed to analyze the thermal properties of the new synthesized polymer. TGA-DSC curves in FIGS. 3B and 3C did not reveal any cold crystallization (Tc) and melting peaks (Tm) appeared in the PXDDA polymers. In the TGA analysis, polymer mass changed with increasing temperature and the results are confined to the oxidation, decomposition, and physical processes like evaporation. As the TGA spectrum of the polymer shows in FIG. 3B (Blue line), there are three steps of weight loss. The weight loss around 200° C. is related to the absorbed moisture in the polymer and a big mass loss step which happened in the region of 280-480° C. was due to polymer degradation and decomposition. The weight loss in the region of 500-580° C. was also attributed to the evaporation of the polymer degradation products. There were three characteristic peaks observed in the DSC curve (Red line) of a PXDDA 1/1 polymer (FIG. 3B). The weight loss in the region of 500-580° C. was also attributed to the evaporation of the polymer degradation products. There were three characteristic peaks observed in the DSC curve (Red line) of a PXDDA 1/1 polymer (FIG. 3(B)). The DSC diagram demonstrated the glass transition temperature (Tg) is around 205° C. The polymer sharp decomposition endothermic peak appeared at about 423° C. and evaporation occurred at about 530° C. By doubling the feeding ratio of DDA, the value of Tg decreased (30-33) (FIG. 3C). The PXDDA 1/2 polymer decomposition peak appeared at a lower temperature and the complete destruction happened in three steps.

2.2. PXDDA Mechanical Properties

Figure 4A:
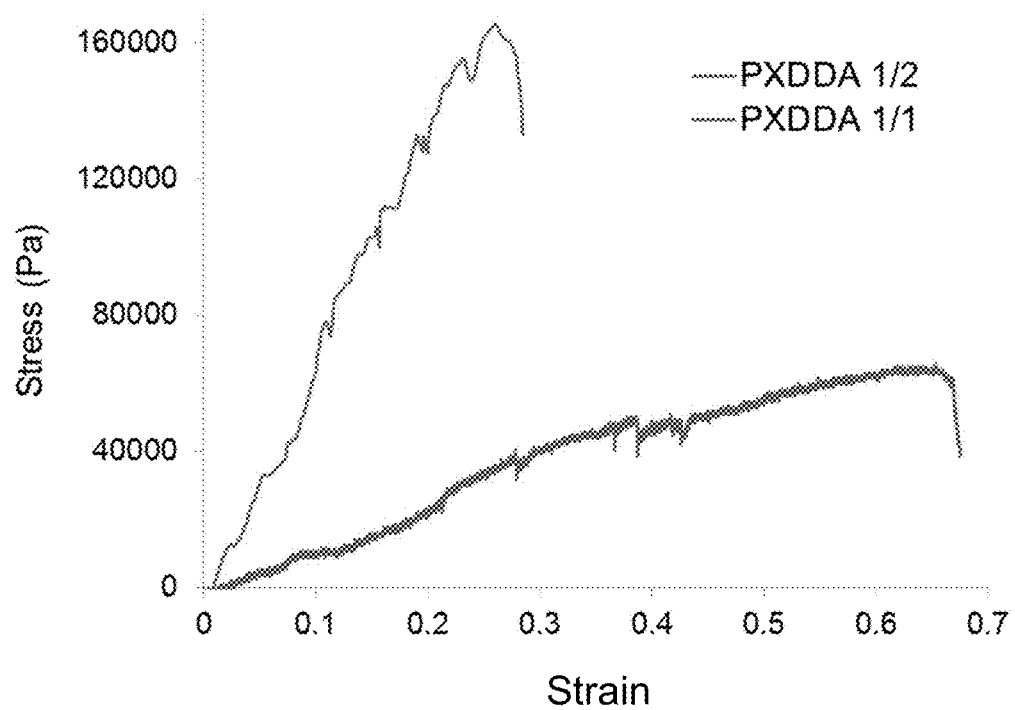
FIG. 4A shows typical stress-strain curves of PXDDA polymers (1/2, 1/1).
Figure 4B:
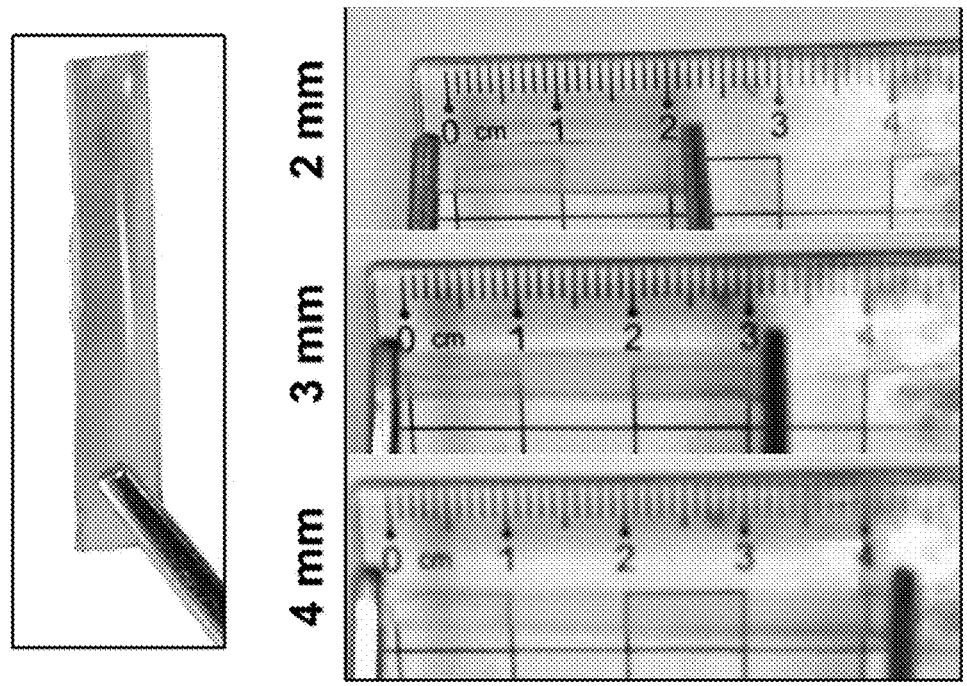
FIG. 4B shows photographs demonstrating the elasticity of an embodiment of PXDDA (1/1).

In order to have a high elasticity and reduce the stress shield from stiff materials to tissues, the mechanical properties of an implantable biomaterials should have an accommodated mechanical property with the surrounding tissue. Tensile test results showed that the synthesized PXDDA 1/1 polymers demonstrate a nonlinear shape of a tensile stress-strain curve, which suggested that the polymer is an elastomeric material (FIG. 4A). The PXDDA polymer had the average tensile Young's modulus of 0.11±0.034 MPa, demonstrating a soft material with elastic properties. Also, the average elongation at rupture and the ultimate tensile strength were 66%±17% and 0.065±0.03 MPa. The PXDDA 1/2 polymer had Young's modulus of 0.69±0.08 MPa, a failure elongation of 27%±8.1% and a UTS of 0.165±0.04 MPa (FIG. 4A). The elasticity decreased with the increasing of DDA. As the grip of the mechanical tester causes stress concentration, the failure will happen at lower strains. Thus, the results only show the minimum elongation, while the total elongation remained unclear. To compensate for this limitation, digital pictures were used to show the elongation of the polymer. Results clearly demonstrated that the PXDDA 1/1 polymer is elastic and stretchable (FIG. 4B). The PXDDA polymer was stretched from its original length of 2 mm to 4 mm without failure. After the external force was released, the polymer can recover to its original length. This result suggested that the elongation before failure is at least 100%. The polymer also showed good stability in cyclic elastic deformation.

The results of the average values obtained from the hardness test showed 35 HA for PXDDA 1/1 and 42 HA for PXDDA 1/2. This hardness result showed that the polymer is a soft material and the hardness increases with the content of DDA in the polymer.

Surface water wettability of the polymer was studied by measuring the contact angle. The water-in-air contact angle values for PXDDA 1/1, 1/2, and PLA are 63.0°±2, 84.0°±3, and 64.0°±2, respectively. This result shows that with the increasing of DDA, the hydrophobicity of PXDDA increased.

2.3. Diffusion Rates of Solvent Molecules in PXDDA

Figure 5A:
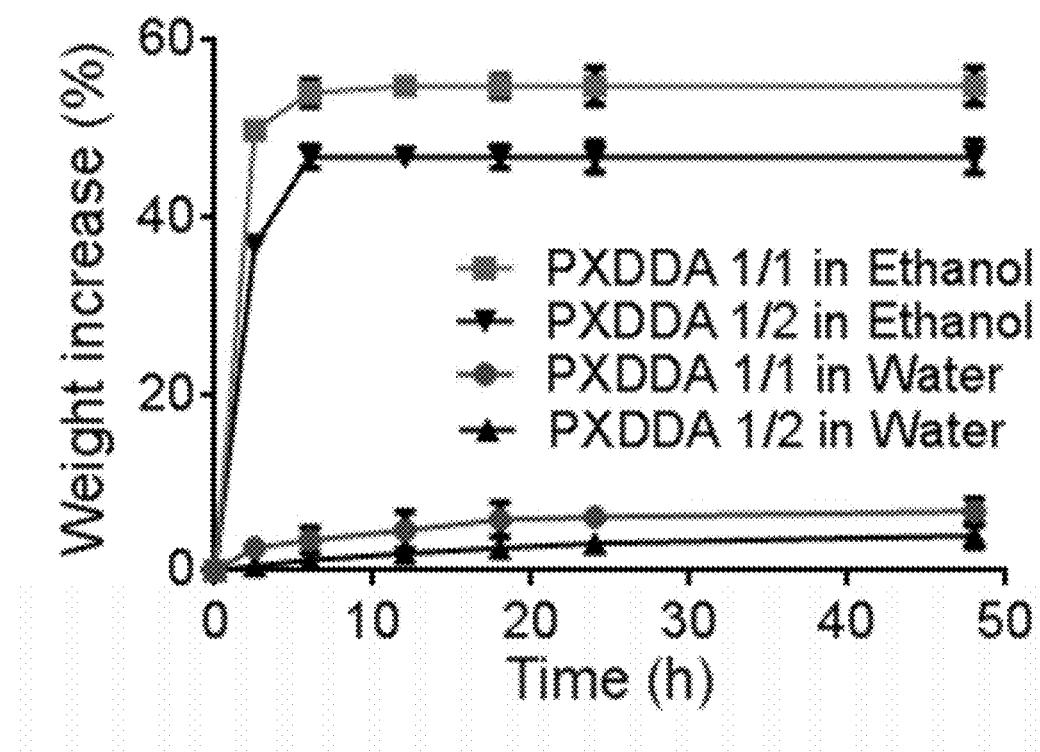
FIG. 5A shows swelling ratios of PXDDA 1/1 and 1/2 versus swelling time in water and ethanol.
Figure 5B:
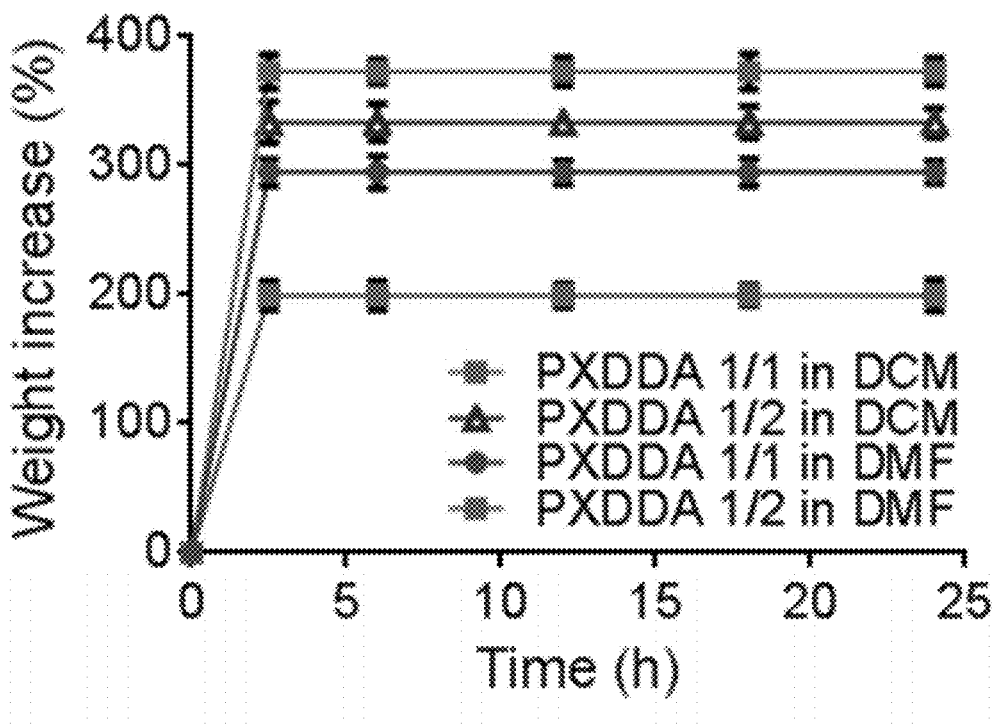
FIG. 5B shows swelling ratios of PXDDA 1/1 and 1/2 versus swelling time in dichloromethane (DCM) and dimethylformamide (DMF).

As mentioned above, the cured polymer was insoluble, but the cross-linked PXDDA swells in water and nonpolar solvents. The swelling measurements indicated reasonable differences in water and other solvents diffusion for various PXDDA polymers. The amount of water absorption in the polymers is small and the mass increasing percentage of PXDDA 1/1 is 6.71% and 3.98% for PXDDA 1/2. Considering different ratios of DDA, the percentage of swelling in ethanol increased 54.08% for PXDDA 1/1 and 46.83% for PXDDA 1/2, respectively (FIG. 5A). For the DMF and DCM solvents (FIG. 5B), the results also confirmed a constant decrease in swelling ratio with the increase in the amount of DDA. The swelling ratio represents the crosslinking degree of the PXDDA structure. The results of swelling experiment confirmed a constant decrease in swelling ratio with the increase in the amount of DDA. The differences are related to the number of hydroxyl groups and hydrophobicity property of the polymer. The swelling decreases with the increase of hydrophobicity. The swelling results also showed the polymer degree of crosslinking.

2.4. In Vitro Release Kinetic of Dyes

In order to study the polymer's ability to release hydrophobic and hydrophilic drugs, RB and RBB dyes as drug models were loaded into the polymer, respectively. Results showed that PXDDA 1/1 samples released 39.72% of RB and 9.46% of RBB within 840 h, whereas only 21.79% and 4.13% release were observed for RB and RBB, respectively in PXDDA 1/2 polymers.

Figure 6A:
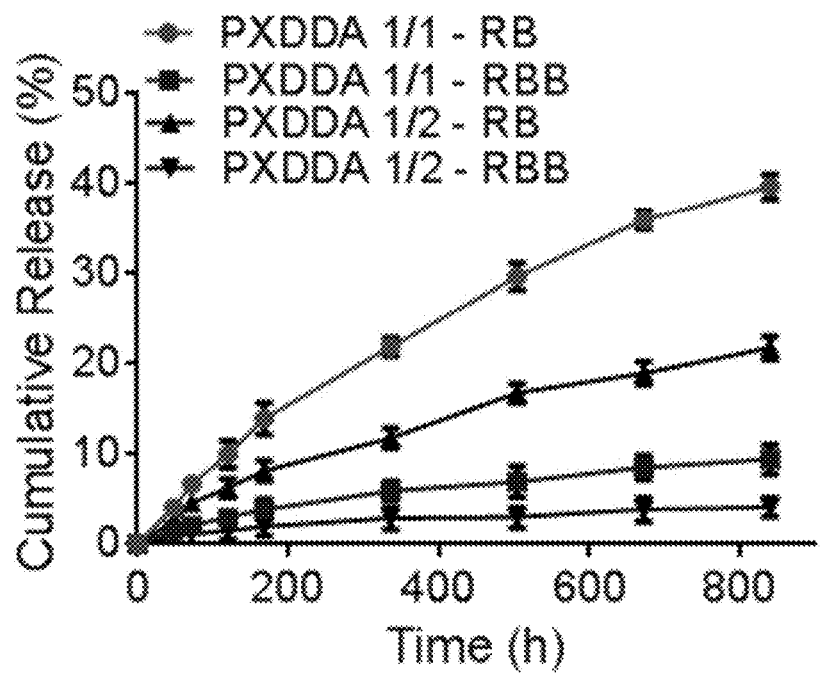
FIG. 6A shows in vitro release profiles of RB and RBB dyes from PXDDA polymers.
Figure 6B:
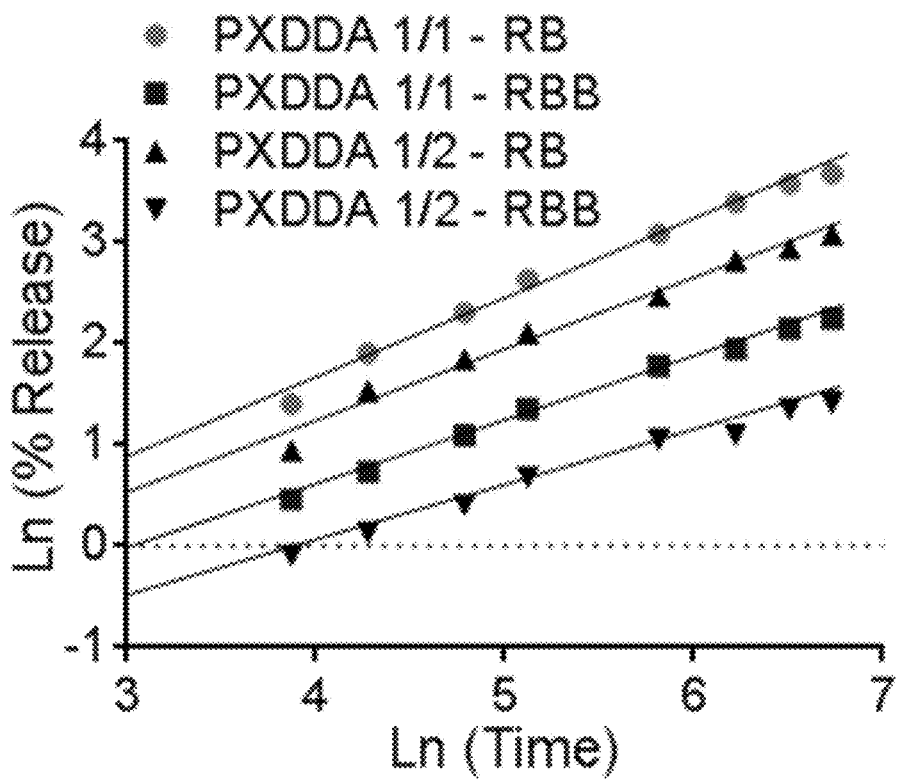
FIG. 6B shows log-log plots of ($Mt/M_\infty$) versus time of RB and RBB release.

To investigate the dye release mechanism, the Korsmeyer-Peppas semi-empirical model was used, which can be shown as $Mt/M_\infty = Kt^n$, $\ln(Mt/M_\infty) = \ln(K) + n \ln t$, where Mt and Mo denote the concentration of a dye released at a specific time duration t and the total amount of dye loaded, respectively. K corresponds to the rate constant, and n signifies the exponent of the release, explaining the possible mechanisms for the dye and drug transport in the structure. Log-log plots of $(Mt/M_\infty)$ with time for RB and RBB released are shown in FIGS. 6A and 6B. All experiments were performed in triplicate and the error bars show a standard deviation.

The obtained values from release profile of RB and RBB for n and k are also shown in Table 2. The polymers will show a non-Fickian/anomalous release behavior if their n values are more than 0.5 (34,35).

TABLE 2 n and k values of dye release of PXDDA polymer

| Polymers | RB k ($h^{-n}$) | RBB k ($h^{-n}$) | RB n | RBB n |
|---|---|---|---|---|
| PXDDA 1:1 | 0.233 | 0.150 | 0.78 | 0.62 |
| PXDDA 1:2 | 0.209 | 0.121 | 0.70 | 0.53 |

2.5. Degradation Behavior of PXDDA

Figure 7A:
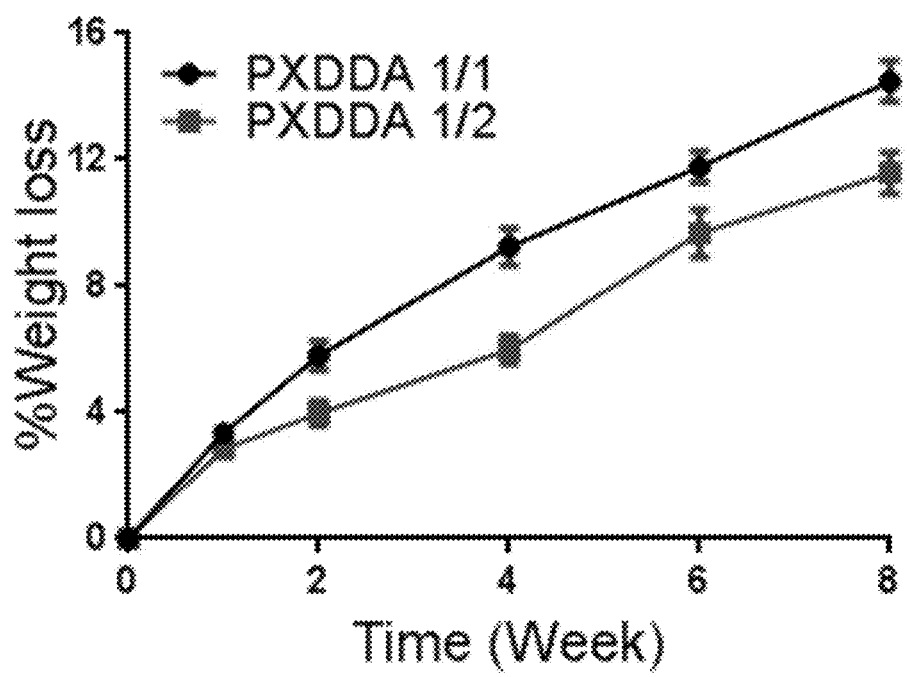
FIG. 7A shows degradation profiles of PXDDA polymers.

In order to have a good correlation between the rates of tissue regeneration and polymer degradation time at the implant site, the polymer's degradation behavior needs to be studied. Two factors can affect the hydrolytic degradation behavior of a polymer. One is related to the presence of hydroxyl groups in the structure, which leads to the further absorption of water molecules into the structure and around the ester bonds. The other is due to the polymer degradation and releasing of acid. As a result, the pH of the environment decreases and affects the hydrolysis rate (36,37). Even so, due to the location of the polymeric scaffolds in the body, the degradation rate can also be increased in vivo by the involvements of enzymes and cells (19). In this study, the degradation profiles of polymers in PBS at 37° C. were analyzed, and the results are shown in FIG. 7A. After two months, the mass of PXDDA 1/1 and 1/2 lost 14.49% and 11.57%, respectively.

Figure 7B:
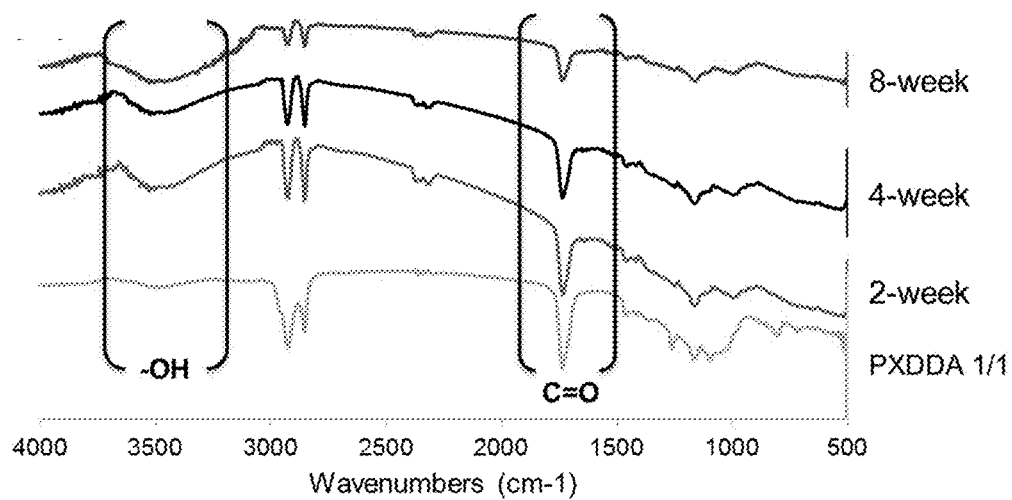
FIG. 7B shows FTIR spectra of a PXDDA 1/1 degradation in different time points. Data are indicated as means±SE with n=3 samples/group.

Also analyzed was the polymer degradation behavior by FTIR and SEM. According to the results of FTIR analysis (FIG. 7B), the intensity of peaks decreased due to the polymer destruction. It is clear that the peak that is related to the ester bonds became less pronounced after 8 weeks of degradation due to the hydrolysis of ester linkages, thus releasing the —OH groups, the related peak of which was more pronounced. FIGS. 8A-8F show the SEM micrographs of PXDDA before and after the degradation. As shown in the SEM images, the surface of the polymer changed from rough to smooth with time, and multiple cracks appeared on it. Separately, the chemical nature of the particles on the polymer surface was detected by the SEM-EDX, which revealed O and C peaks (FIGS. 8G and 8H).

2.6. Auto-Fluorescent Property

Fluorescence is a phenomenon in which a particular material is stimulated after exposure to visible or non-visible light or heat. The material stores the energy in itself, and then emits it as a spectrum of visible waves over time. The durability of radiation is different for various biomedical engineering applications (38,39). The new PXDDA developed herein shows characteristic fluorescence properties that make it applicable to different areas of new technologies, bioengineering, molecular biology, genomics, biomedical diagnosis, medicine, biological research, proteomics, and industrial microbiology (38,40). Due to the cavity and branch structure, PXDDA polymer has the ability to carry medications and various chemical molecules, and ultimately its fluorescence property provides imaging for drug tracing (39,41). FIGS. 9A, 9B and 9C display the different fluorescence microscope images of a PXDDA polymer. The fluorescent PXDDA films can emit various ranges of colors under the excitation of a visible light, including blue light (400-500 nm), green light (500-550 nm) and red light (550-650 nm). FIG. 9D also demonstrates the fluorescence emission spectra of PXDDA polymer for three different excitation wavelengths. The PXDDA polymer has a wide range of fluorescence from around 420 to 720 nm with a maximum emission of around 520 nm. The fluorescence emission of PXDDA films is related to the variation of C═O and C—O bonds in the prepolymer and polymer structures. This property came from the C═O linkages in the polymeric chain which were generated during the curing process. As a control, PLA was exposed to the same tests. As shown in FIG. 9E, PLA demonstrated no auto-fluorescence.

2.7. Biocompatibility of PXDDA Discs

In order to investigate whether the new synthesized PXDDA polymer can be used in tissue regeneration, its biocompatibility was first tested by using endothelial cells. Results showed that cells significantly proliferated on PXDDA compared with the PLA (material control) and control group at different incubation times (FIG. 10A). The MTT cell viability assay proved that proliferation rate increased with time for all groups, and cells proliferated even faster on PXDDA polymers than on PLA and tissue culture plate control groups. No tangible toxicity was detected at different concentrations of degradation products after 36 h (FIG. 10B). Three concentrations of the products from the two types of PXDDA polymers were examined. Results show that there is no significant difference in cell proliferation between the two types of PXDDA polymers and well-plates. It was clearly demonstrated that the PXDDA and its degraded products have no toxicity to cells in vitro.

The morphology of HUVEC cells cultured on the PXDDA discs was assessed by SEM, as shown in FIG. 10C. The morphology of HUVEC cells grown on PLA is shown in FIG. 10E. Generally, HUVEC cells have an elongated morphology in a monolayer on surfaces of a tissue culture plate (FIG. 10D). In contrast, it is revealed from the SEM micrographs that the cells on PXDDA polymer aggregated to grow on the surface. This morphology may be attributed to the polymer surface properties. Cell proliferation results confirmed that polymers are non-toxic compared with TCP and PLA (1,9,42,43).

2.8 Characterization of Polydopamine-Coated PXDDA

To load growth factors onto the surface of the PXDDA disc, a dopamine coating method was used (FIG. 11A). Before and after coating, the morphology and microstructure of the PXDDA with dopamine coating was also observed using a SEM. Before coating, we can see that the surface of the PXDDA disc is smooth. After coating, the dopamine-coated PXDDA surface showed that many particles were formed on the surface completely and increased the surface roughness as well (FIGS. 11B and 11C). Dopamine's crystal forms were identified with XRD patterns. The XRD pattern for the polydopamine-coated PXDDA in FIG. 11D shows the existence of dopamine loaded on PXDDA surface. The broad reflection peak at 19.58° could be assigned to the amorphous structures of dopamine diffraction.

To study the chemical structure of the coated PXDDA surface, FTIR spectroscopy was used. According to FIG. 11E, the spectrum of polydopamine-coated PXDDA demonstrates well-defined characteristic bonds which also exist in the uncoated PXDDA spectrum with a relative different intensity which means that the coating process does not affect the PXDDA properties and surface chemical structure. The absorption band at 3456 $cm^{-1}$, which attributes to the stretching vibrations of —OH groups in the PXDDA, broadened and underwent a small shift to 3392 $cm^{-1}$ for polydopamine-coated PXDDA. Such characteristics are corresponded to the aromatic—C—OH bonding in dopamine. The sharp peaks at 1728 $cm^{-1}$ and 1159 $cm^{-1}$ are also assigned to the C—O and C—O bonds, respectively.

Figure 12:
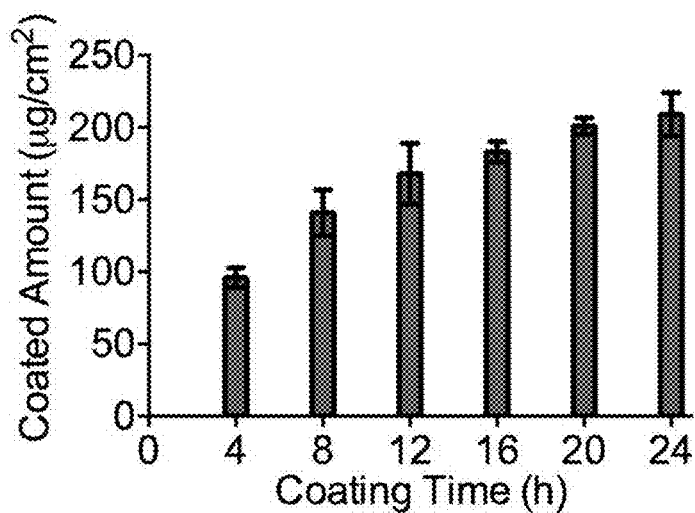
FIG. 12 shows amounts of polydopamine coated on the PXDDA discs determined using BCA.

According to BCA assay results in FIG. 12, the amount of dopamine on PXDDA surface increased from 96 to 183 $\mu g/cm^2$ as coating time increased from 4 h to 16 h. It confirmed that the amount of polydopamine coated on PXDDA films is time-dependent. The coating reaction relies on the reduction of copper ions with proteins in the alkaline medium ($Cu^{2+}$ to $Cu^{1+}$), which can be gotten from the dopamine's catecholamine group. Covalent and non-covalent interactions like electrostatic, hydrogen bonding, and π-π interactions exist between the polydopamine coating and the PXDDA films.

2.9 Quantification of Immobilized Growth Factor and In Vitro Release Profile

Figure 13:
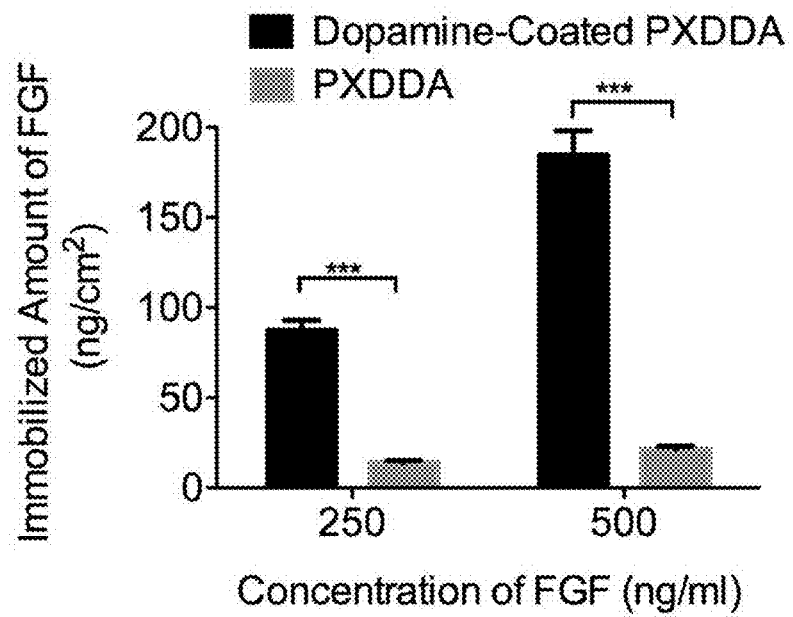
FIG. 13 shows the quantification of FGF immobilized on polydopamine-coated PXDDA discs using ELISA.

The binding efficiency and growth factor release profiles of FGF on polydopamine-coated and uncoated PXDDA discs were defined by ELISA. As FIG. 13 shows, the FGF binding efficiency of the polydopamine-coated disc is higher than that of the uncoated PXDDA disc. The efficiency of FGF immobilization on polydopamine-coated PXDDA discs is approximately 6.2 (250 ng/ml) and 8.5 (500 ng/mL) times higher than that on PXDDA discs without polydopamine coating. The ELISA results also demonstrated that the amount of immobilized growth factor on polydopamine-coated PXDDA increased by increasing the concentration of growth factor in treatment solutions. When 500 µL of FGF with different concentrations of 250 ng/mL and 500 ng/mL were used to treat each $cm^2$ of polydopamine-coated discs, the polydopamine-coated group which was treated with 500 ng/mL of FGF, demonstrated more immobilized FGF (184.67 ng/cm2) than the other group (87.33 ng/cm2). These results confirmed that the polydopamine coating on the surface of polymeric discs would effectively improve the binding efficiency of growth factors to the surface.

Figure 14:
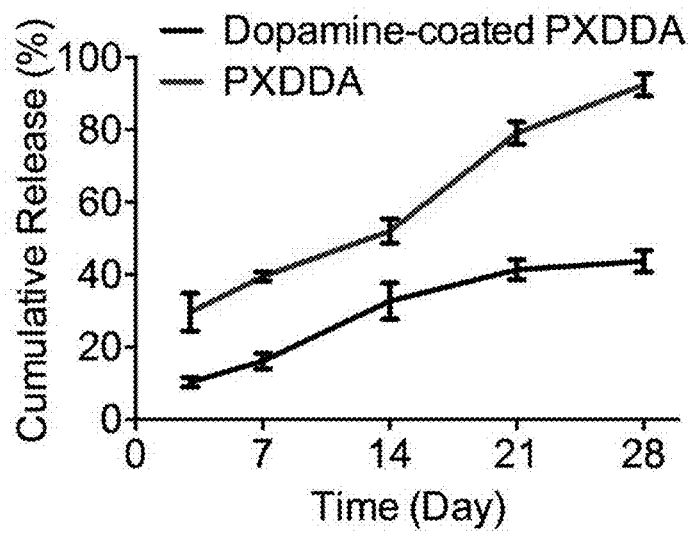
FIG. 14 shows release profile of Fibroblast Growth Factor (FGF).

In vitro release profile of growth factor from the grafted surface also indicated that there was a release with 41% and 79% of the total FGF released from the polydopamine-coated and uncoated PXDDA discs within 21 days, respectively (FIG. 14). After 28 days, around 67% of the growth factor was stably retained on the coated PXDDA surface, which confirmed that the dopamine could sustain release. The release results showed that the polydopamine coating increased the amount of the immobilized growth factors on the PXDDA surface and decreased the growth factor release. As a conclusion, the immobilized growth factor could have a sustained release rate.

2.10 Adhesion and Proliferation of Fibroblast Cells

Figure 15:
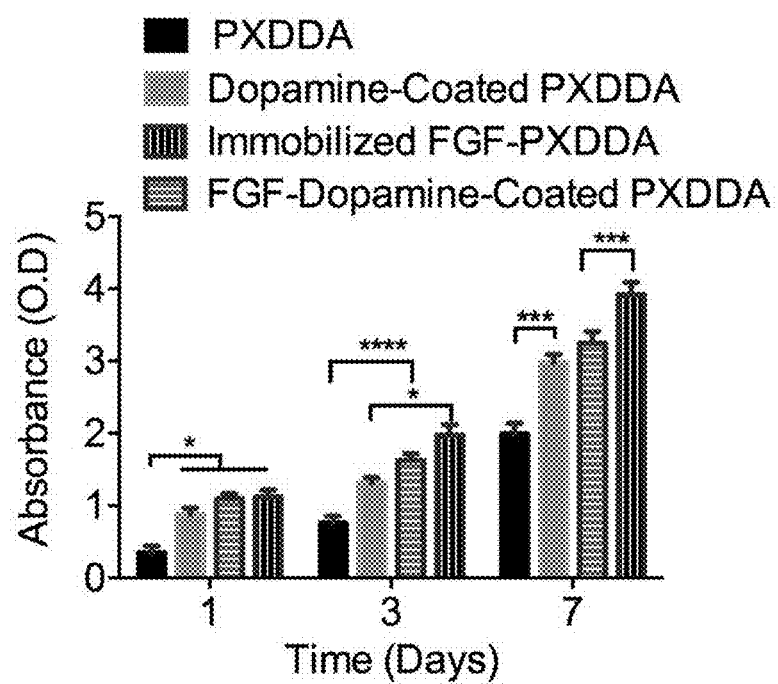
FIG. 15 shows MTT assay results of fibroblast cells culture.
Figure 16A:
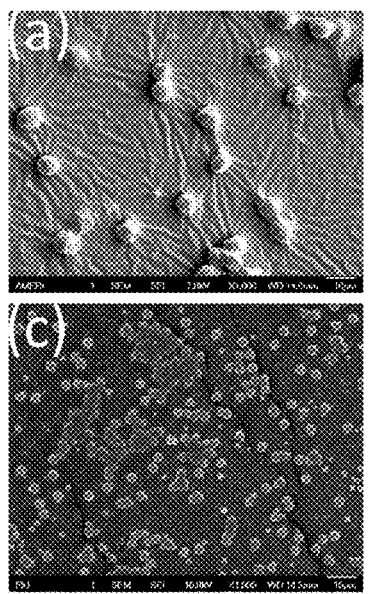
FIG. 16A is an SEM micrograph of fibroblast cells on uncoated PXDDA.
Figure 16B:
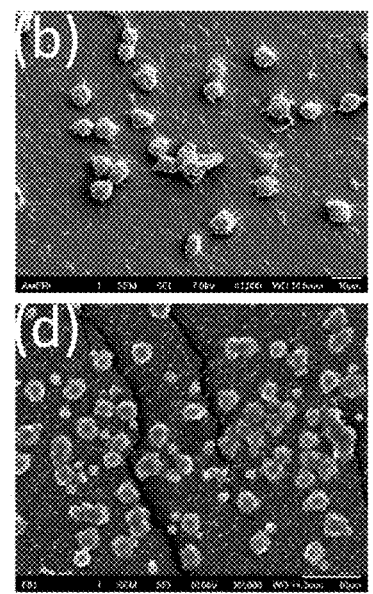
FIG. 16B is an SEM micrograph of fibroblast cells on uncoated PXDDA.

As shown in FIG. 15, the seeded fibroblast cells on the untreated PXDDA discs, indicated the lowest cell viability. After dopamine coating, the viability of cells was significantly increased in the polydopamine-coated PXDDA discs compared to uncoated PXDDA. As we mentioned earlier, dopamine coating increased the surface roughness, which could have positive effects on the cell adhesion. On the other hand, the hydroxyl and amine groups of dopamine also promote the cell adhesion and proliferation. When the fibroblast cells were cultured on the FGF-immobilized PXDDA discs, the absorbance significantly increased. The growth factor has an important role in improving tissue regeneration as it increases adhesion, proliferation, and differentiation. While cells were seeded on the FGF-immobilized dopamine-coated PXDDA disc, cells significantly proliferated. These results confirm that the immobilization of fibroblast growth factor on dopamine-coated PXDDA significantly improved cells viability. SEM images showed that the fibroblast cells showed less cell adhesion and spreading at 7 days on uncoated PXDDA films (FIGS. 16A and 16B), while fibroblast cells morphology on FGF-polydopamine-coated PXDDA discs after 7 days of culture attached more and proliferated significantly (FIGS. 16C and 16D).

3. Discussion

The interest in soft tissue regeneration has increased the efforts to synthesize new polymers with modulated biodegradable and elastic properties. This study reports the synthesis of a biocompatible, elastic and auto-fluorescent polyester with potential applications in tissue engineering. Its degradation rate and mechanical properties can be adjusted by changing the molar ratio of monomers and curing time. The PXDDA pre-polymer is relatively viscous and it can be dissolved in many organic solvents such as ethanol, THF, DMF, dioxane, and chloroform, so it can be molded into different shapes from sheets to complex 3D structures.

In this study, it was found that the solidified characteristic and properties of PXDDA are tightly related to the contents of DDA monomers. The pre-polymer NMR results confirmed the relationship between polymer building blocks and the monomer ratios in the polymer structure. The intermolecular interactions caused by the different contents of functional groups changed the intensity of the peaks in FTIR for PXDDA with different ratios. The peak for C=O in PXDDA 1/2 showed more intense compared to that in PXDDA 1/1, as its ester bonds density is higher due to the larger amount of DDA. It is also obvious that the intensity of the —OH peak decreased with the DDA ratio increasing, as the acidity enhanced, the hydrogen atoms of hydroxyl groups reacted more and fewer unreacted hydroxyl remained in the structure. The XRD analysis indicated that the PXDDA is amorphous. DSC results also confirmed the amorphous state of PXDDA, which makes this biomaterial potential candidate for implantable tissue-engineering scaffolds, as amorphous state of a polymer brings faster degradation rate relative to a crystalline polymer. The absence of melting and crystallization peaks in the DSC graphs indicated that all the monomers have fully participated in the reaction and formed the cross-linked structure. On the other hand, the high glass transition temperature of PXDDA demonstrates that the polymer state will not change at room and physiological temperature. By doubling the feeding ratio of DDA, the number of —COOH groups increased in the reaction. Thus, they reacted with more —OH groups in xylitol to form more ester linkages. As a result, the polymer structure became more hydrophobic and consequently, Tg decreased (FIG. 3C).

This study fabricated a new polymer, and this polymer has high elasticity, one important property. Elastic fibers are one of the main components of extracellular matrix (ECM) whose function is providing mechanical elasticity for tissues. For example, the elastic fibers help the expansion and contraction of arteries, so they can control the changes in blood pressure.

Therefore, the biomaterials used in soft tissue regeneration require elastic properties at some a degree, so that they can be deformed under the physiological forces and thus gradually release their stored energy (17,44). Tensile test results in this study showed that increasing the ratio of the DDA monomer caused higher crosslink density, which increased the stiffness of the synthesized polymer. For instance, compared with PXDDA 1/1, the PXDDA 1/2 had a lower failure strain and higher modulus. At the same time, increasing the content of DDA monomer in the polymer composition also affects the hardness and stiffness of final PXDDA polymer. Additionally, the increase of the cross-linking density reduced the degradation rate. Collectively, in order to obtain a balance between the mechanical properties and the degradation rate, adjusting the amount of DDA in the structure or curing time would be a feasible strategy.

The hydrophilicity of a polymer is an important property for cell attachment. In this study it is clear that the values of contact angle increased with the addition of more DDA monomer in the polymer. This result is due to the increasing hydrophobicity. More aliphatic DDA monomers in the structure increased the hydrophobicity. In fact, with the DDA content increasing, the number of hydroxyl groups that are attached to the backbone decreased, resulting in the increased hydrophobicity. Therefore, the hydrophobicity depends on the two aspects of DDA contents and residual hydroxyl groups. These contact angle data are consistent with the results of FTIR, as the hydroxyl groups have a noted stretching peak for PXDDA 1/1 but it is completely absent for PXDDA 1/2.

The wide applied field of a biodegradable polymer is in drug delivery system. Some factors of a polymer may affect the release rate of drugs from a biodegradable polymer, like hydrophilicity, diffusion, hydrolytic degradation, cross-linking degree, porosity, drug molecules size, drug solubility in dispersion media, uniformity of drug dispersion inside the polymer structure, bonding's nature between polymer and drug, etc. (45-47). In this study, model dyes, RBB and RB first, were used to examine the control release ability of PXDDA on drugs. Generally, RBB is released slower than RB due to the presence of more hydrophilic groups in RB. As a result, less hydrophobic interactions in RB in comparison with RBB. In other words, since the polymer nature is hydrophobic and the surrounding environment is hydrophilic, RB is released faster due to the tendency towards the water. Just as it was mentioned before, hydrophobicity increased by increasing the ratio of DDA and cross-link density, which led to the reduction in degradation rate. As a result, RB and RBB release rate and k value decreased for PXDDA 1/2. The release results were also consistent with the results of wettability, swelling and degradation. As the release rate of dye is sustained and controlled by the PXDDA polymer, it could be applicable in sustained drug delivery applications.

Then, we loaded a growth factor FGF to verify the ability of the coating on the polymer to release. Growth factor delivery systems based on biomaterials (inorganic, natural, or synthetic) with different structures are able to make differential immobilization efficiency and release kinetics in the local environment. These new biomaterial systems are still in the preliminary steps of laboratory research and development and need more solid clinical data. One of the most significant challenges in this area for promoting tissue regeneration is related to adequate growth factor concentrations and gradients. The instant invention comprised the development of PXDDA films modified using polydopamine-assisted immobilization of FGF through a simple coating process. The polydopamine coating on the PXDDA films enhanced the binding sites to growth factor, and FGF bound on the PXDDA surface slowly released over 30 days in vitro. In vitro studies showed that the FGF-polydopamine-PXDDA films have a significant role for supporting adhesion, spreading, and proliferation of fibroblast cells. Quantification of FGF on coated PXDDA films showed that increasing the amount of FGF in the treatment solution, enhanced the level of immobilized FGF. Studies with fibroblast cells also indicated initial adhesion and proliferation of cells cultured on PXDDA films modified with FGF.

In addition to the study of the drug release ability of the polymer, studying the polymer's degradation behavior is necessary. The difference in the degradation rate of PXDDA polymers is related to the molar ratio of DDA. In fact, increasing the amount of DDA causes a reduction in the degradation rate of a polymer, which is attributed to the higher cross-linking density and hydrophobicity, and lower diffusion coefficient that is resistant against water penetration and hydrolysis. On the other hand, since the degradation of the polymer depends on the degradation of the ester bonds, the rate of degradation is reduced by the increased concentration of the ester bonds due to the increase of DDA in the polymer (48,49). From the EDX results, it can be implied that there is no phase separation in the structure and the polymer network is uniform. In thin polymeric films, the degree of separation can change the polymer morphology which may cause undesired effects on the properties of the resulting film. The PXDDA is mainly undergoing surface degradation, as the size of the PXDDA discs in the degradation solution shrunk down (data not shown). Thus, its mechanical properties may gradually decrease, which is an advantage when compared to materials that are degrading through bulk degradation such as PGA, PLGA, and PLA. Therefore, the PXDDA can keep predictable mechanical properties in the period of degradation.

The fluorescent properties of the newly synthesized PXDDA polymer are an unexpected and significant benefit. In general, petroleum-based materials, like polypropylene and polyamide, are used for fluorescent fibers. However, in comparison with the bio-based materials like PLA (39), they are not economical. Biodegradability, biocompatibility and renewability are the factors which make biomaterials attractive in this field (38,39). Fluorescence is an additional valuable factor that make a polymer more attractive for the applications in bioengineering, molecular biology, genomics, diagnosis, biological research, proteomics, and industrial microbiology (38,40). Due to its cavity and branch structure, PXDDA polymer has the ability to carry drugs and various chemical molecules and release them, while its fluorescence property additionally enables one to track the release of drugs or molecules without the use of other tracking fluorescent dyes (39,41).

The most important property of this new elastic polymer is its biological property, since it will be applied in tissue engineering. Our study found that cell proliferation on PXDDA was faster compared to the PLA control, showing that PXDDA has better ability to promote cell proliferation than PLA, one of the most widely used biodegradable polymer in biomedical applications (28,29). PXDDA indicated significant cell-promoting ability and excellent biocompatibility in vitro. This biological function of PXDDA may be attributed to the presence of xylitol in the polymer composition, because studies have shown that xylitol enhances cell growth and proliferation. Xylitol also has immunomodulatory, anti-bacterial, and anti-phagocytic properties (4,25). As inflammatory chemicals are released from injured tissue cells, xylitol-based materials with anti-inflammatory effects can be excellent candidates for tissue regeneration (21). Furthermore, studies showed that xylitol promoted bone metabolism (50). This property makes PXDDA a good candidate for use in bone tissue regeneration.

This study demonstrates the value of a new polymer synthesized from renewable resources, which has multiple desirable properties, including adjustable mechanical properties, elasticity, biodegradability, auto-fluorescent property, and significant cell-promoting function. PXDDA shows great promise as a material for use in tissue regeneration (such as for intervertebral discs, cornea, bone, and small diameter arteries (4,51-53) and in other medical and non-medical applications where its unique combination of properties will be of great value.

Additionally, this study uses a simple, mild coating method of dopamine to graft growth factors onto the surface.

The FGF-loaded polymer also demonstrated better cell viability.

We successfully synthesized and characterized PXDDA elastomers with different molar ratios for potential uses in tissue regeneration and drug delivery system. The melt condensation polymerization provides a simple and inexpensive route for the synthesis of biocompatible and biodegradable polymers with a wide range of tunable properties based on the monomer ratios and curing time. According to the results, the monomer ratios have significant effects on degradation and mechanical properties. Contact angle, hardness, Young's modulus, and stiffness increased with an increase in molar ratio of dodecanedioic acid and consequently crosslink density, whereas glass-transition temperature, swelling, degradation and dye release decreased. Further, this new polymer showed auto-fluorescence property with continuous blue, green, and red light illumination under the fluorescence microscope. Biocompatibility studies also indicated that the PXDDA polymer and related degraded products are not cytotoxic. Compared with the other ester polymer classes, PXDDA showed a better potential for cell adhesion and proliferation. Growth factor loaded polymers showed better in vitro drug release profile. Polydopamine coating is a cheap, simple, and effective method for GF immobilization onto the biomaterial surfaces, and the FGF immobilized polydopamine-PXDDA films are a promising candidate for guided tissue regeneration.

While the invention has been described in detail and with reference to specific examples thereof, it will be apparent to one skilled in the art that various changes and modifications can be made therein without departing from the spirit and scope thereof.

REFERENCES CITED (1) Kolanthai, E.; Sarkar, K.; Meka, S. R. K.; Madras, G.; Chatterjee, K. Copolyesters from Soybean Oil for Use as Resorbable Biomaterials. *ACS Sustain. Chem. Eng.* 2015, 3 (5), 880-891. https://doi.org/10.1021/acssuschemeng.5b00001.

(2) Yang, J.; Webb, A. R.; Ameer, G. A. Novel Citric Acid-Based Biodegradable Elastomers for Tissue Engineering. *Adv. Mater.* 16 (6), 511-516. https://doi.org/10.1002/adma.200306264.

(3) Rezayan, A. H.; Firoozi, N.; Kheirjou, S.; Tabatabaei Rezaei, S. J.; Nabid, M. R. Synthesis and Characterization of Biodegradable Semi-Interpenetrating Polymer Networks Based on Star-Shaped Copolymers of ε-Caprolactone and Lactide. *Iran. J. Pharm. Res.* IJPR 2017, 16 (1), 63-73.

(4) Bruggeman, J. P.; Bettinger, C. J.; Nijst, C. L. E.; Kohane, D. S.; Langer, R. Biodegradable Xylitol-Based Polymers. *Adv. Mater.* 2008, 20 (10), 1922-1927. https://doi.org/10.1002/adma.200702377.

(5) Bhattarai, D. P.; Aguilar, L. E.; Park, C. H.; Kim, C. S. A Review on Properties of Natural and Synthetic Based Electrospun Fibrous Materials for Bone Tissue Engineering. *Membranes* 2018, 8 (3). https://doi.org/10.3390/membranes8030062.

(6) Maitz, M. F. Applications of Synthetic Polymers in Clinical Medicine. *Biosurface Biotribology* 2015, 1 (3), 161-176. https://doi.org/10.1016/j.bsbt.2015.08.002.

(7) Li, Y.; Huang, W.; Cook, W. D.; Chen, Q. A Comparative Study on Poly(Xylitol Sebacate) and Poly(Glycerol Sebacate): Mechanical Properties, Biodegradation and Cytocompatibility. *Biomed. Mater. Bristol Engl.* 2013, 8 (3), 035006. https://doi.org/10.1088/1748-6041/8/3/035006.

(8) Tran, R.; Dey, J.; Gyawali, D.; Zhang, Y.; Yang, J. Biodegradable Elastomeric Polymers and MEMS in Tissue Engineering. In *Biomaterials for MEMS*; Chiao, J.-C., Ed.; Pan Stanford Publishing, 2011. https://doi.org/10.1201/b11116-4.

(9) Natarajan, J.; Madras, G.; Chatterjee, K. Maltitol-Based Biodegradable Polyesters with Tailored Degradation and Controlled Release for Bone Regeneration. *RSC Adv.* 2016, 6 (46), 40539-40551. https://doi.org/10.1039/C6RA02058E.

(10) Natarajan, J.; Madras, G.; Chatterjee, K. Development of Graphene Oxide-/Galactitol Polyester-Based Biodegradable Composites for Biomedical Applications. *ACS Omega* 2017, 2 (9), 5545-5556. https://doi.org/10.1021/acsomega.7b01139.

(11) Wu, L.; Mincheva, R.; Xu, Y.; Raquez, J.-M.; Dubois, P. High Molecular Weight Poly(Butylene Succinate-Co-Butylene Furandicarboxylate) Copolyesters: From Catalyzed Polycondensation Reaction to Thermomechanical Properties. *Biomacromolecules* 2012, 13 (9), 2973-2981. https://doi.org/10.1021/bm301044f.

(12) Firoozi, N.; Rezayan, A. H.; Rezaei, S. J. T.; Mir-Derikvand, M.; Nabid, M. R.; Nourmohammadi, J.; Arough, J. M. Synthesis of Poly(ε-Caprolactone)-Based Polyurethane Semi-Interpenetrating Polymer Networks as Scaffolds for Skin Tissue Regeneration. *Int. J. Polym. Mater. Polym. Biomater.* 2017, 66 (16), 805-811. https://doi.org/10.1080/00914037.2016.1276059.

(13) Saini, P.; Arora, M.; Kumar, M. N. V. R. Poly(Lactic Acid) Blends in Biomedical Applications. *Adv. Drug Deliv. Rev.* 2016, 107, 47-59. https://doi.org/10.1016/j.addr.2016.06.014.

(14) Malikmammadov, E.; Tanir, T. E.; Kiziltay, A.; Hasirci, V.; Hasirci, N. PCL and PCL-Based Materials in Biomedical Applications. *J. Biomater. Sci. Polym. Ed.* 2018, 29 (7-9), 863-893. https://doi.org/10.1080/09205063.2017.1394711.

(15) Gentile, P.; Chiono, V.; Carmagnola, I.; Hatton, P. V. An Overview of Poly(Lactic-Co-Glycolic) Acid (PLGA)-Based Biomaterials for Bone Tissue Engineering. *Int. J. Mol. Sci.* 2014, 15 (3), 3640-3659. https://doi.org/10.3390/ijms15033640.

(16) Hiob, M. A.; Crouch, G. W.; Weiss, A. S. Elastomers in Vascular Tissue Engineering. *Curr. Opin. Biotechnol.* 2016, 40, 149-154. https://doi.org/10.1016/j.copbio.2016.04.008.

(17) Davenport Huyer, L.; Zhang, B.; Korolj, A.; Montgomery, M.; Drecun, S.; Conant, G.; Zhao, Y.; Reis, L.; Radisic, M. Highly Elastic and Moldable Polyester Biomaterial for Cardiac Tissue Engineering Applications. *ACS Biomater. Sci. Eng.* 2016, 2 (5), 780-788. https://doi.org/10.1021/acsbiomaterials.5b00525.

(18) Li, Y.; Thouas, G. A.; Shi, H.; Chen, Q. Enzymatic and Oxidative Degradation of Poly(Polyol Sebacate). *J. Biomater. Appl.* 2014, 28 (8), 1138-1150. https://doi.org/10.1177/0885328213499195.

(19) Wang, Y.; Ameer, G. A.; Sheppard, B. J.; Langer, R. A Tough Biodegradable Elastomer. *Nat. Biotechnol.* 2002, 20 (6), 602-606. https://doi.org/10.1038/nbt0602-602.

(20) Dasgupta, Q.; Chatterjee, K.; Madras, G. Combinatorial Approach to Develop Tailored Biodegradable Poly(Xylitol Dicarboxylate) Polyesters. *Biomacromolecules* 2014, 15 (11), 4302-4313. https://doi.org/10.1021/bm5013025.

(21) Ur-Rehman, S.; Mushtaq, Z.; Zahoor, T.; Jamil, A.; Murtaza, M. A. Xylitol: A Review on Bioproduction, Application, Health Benefits, and Related Safety Issues. *Crit. Rev. Food Sci. Nutr.* 2015, 55 (11), 1514-1528. https://doi.org/10.1080/10408398.2012.702288.

(22) Moschouris, K.; Firoozi, N.; Kang, Y. The Application of Cell Sheet Engineering in the Vascularization of Tissue Regeneration. *Regen. Med.* 2016, 11 (6), 559-570. https://doi.org/10.2217/rme-2016-0059.

(23) Wong et al. A novel poly(xylitol-co-dodecanedioate)/hydroxyapatite composite with shape-memory behaviour—ScienceDirect, 2014 https://www.sciencedirect.com/science/article/pii/S0167577X14005783 (accessed Apr. 23, 2018).

(24) Selvam, S.; Pithapuram, M. V.; Victor, S. P.; Muthu, J. Injectable in Situ Forming Xylitol-PEG-Based Hydrogels for Cell Encapsulation and Delivery. *Colloids Surf. B Biointerfaces* 2015, 126, 35-43. https://doi.org/10.1016/j.colsurfb.2014.11.043.

(25) Albarran-Preza, E.; Corona-Becerril, D.; Vigueras-Santiago, E.; Hernandez-López, S. Sweet Polymers: Synthesis and Characterization of Xylitol-Based Epoxidized Linseed Oil Resins. *Eur. Polym. J.* 2016, 75, 539-551. https://doi.org/10.1016/j.eurpolymj.2015.12.025.

(26) Solorio, L. D.; Bocks, M. L.; Hollister, S. J. Tailoring the Physicochemical and Shape Memory Properties of the Biodegradable Polymer Poly(Glycerol Dodecanoate) via Curing Conditions. *J. Biomed. Mater. Res. A* 2017, 105 (6), 1618-1623. https://doi.org/10.1002/jbm.a.35973.

(27) Migneco, F.; Huang, Y.-C.; Birla, R. K.; Hollister, S. J. Poly(Glycerol-Dodecanoate), a Biodegradable Polyester for Medical Devices and Tissue Engineering Scaffolds. *Biomaterials* 2009, 30 (33), 6479-6484. https://doi.org/10.1016/j.biomaterials.2009.08.021.

(28) Madhavan Nampoothiri, K.; Nair, N. R.; John, R. P. An Overview of the Recent Developments in Polylactide (PLA) Research. *Bioresour. Technol.* 2010, 101 (22), 8493-8501. https://doi.org/10.1016/j.biortech.2010.05.092.

(29) Jamshidian, M.; Tehrany, E. A.; Imran, M.; Jacquot, M.; Desobry, S. Poly-Lactic Acid: Production, Applications, Nanocomposites, and Release Studies. *Compr. Rev. Food Sci. Food Saf.* 9 (5), 552-571. https://doi.org/10.1111/j.1541-4337.2010.00126.x.

(30) Chung, H.-J.; Woo, K.-S.; Lim, S.-T. Glass Transition and Enthalpy Relaxation of Cross-Linked Corn Starches. *Carbohydr. Polym.* 2004, 55 (1), 9-15. https://doi.org/10.1016/j.carbpol.2003.04.002.

(31) Hirose, S.; Hatakeyama, T.; Hatakeyama, H. Glass Transition and Thermal Decomposition of Epoxy Resins from the Carboxylic Acid System Consisting of Ester-Carboxylic Acid Derivatives of Alcoholysis Lignin and Ethylene Glycol with Various Dicarboxylic Acids. *Thermochim. Acta* 2005, 431 (1), 76-80. https://doi.org/10.1016/j.tca.2005.01.043.

(32) Prucker, O.; Christian, S.; Bock, H.; Ruhe, J.; Frank, C. W.; Knoll, W. On the Glass Transition in Ultrathin Polymer Films of Different Molecular Architecture. *Macromol. Chem. Phys.* 1998, 199 (7), 1435-1444. https://doi.org/10.1002/(SICI)1521-3935(19980701)199:7<1435::AID-MACP1435>3.0.CO;2-#.

(33) Khonakdar, H. A.; Morshedian, J.; Wagenknecht, U.; Jafari, S. H. An Investigation of Chemical Crosslinking Effect on Properties of High-Density Polyethylene. *Polymer* 2003, 44 (15), 4301-4309. https://doi.org/10.1016/S0032-3861(03)00363-X.

(34) Costa, P.; Sousa Lobo, J. M. Modeling and Comparison of Dissolution Profiles. *Eur. J. Pharm. Sci.* 2001, 13 (2), 123-133. https://doi.org/10.1016/SO928-0987(01)00095-1.

(35) Natarajan et al. Polyanhydrides of Castor Oil-Sebacic Acid for Controlled Release Applications—Industrial & Engineering Chemistry Research (ACS Publications), 2014 https://pubs.acs.org/doi/abs/10.1021/ie500679u (accessed Jun. 6, 2018).

(36) Engineer et al. *Review on Hydrolytic Degradation Behavior of Biodegradable Polymers from Controlled Drug Delivery System. Trends in Biomaterials & Artificial Organs,* 2011, http://connection.ebscohost.com/c/articles/67149801/review-hydrolytic-degradation-behavior-biodegradable-polymers-from-controlled-drug-delivery-system (accessed Jun. 6, 2018).

(37) Li, J.; Washington, M. A.; Bell, K. L.; Weiss, R. M.; Rothstein, S. N.; Little, S. R.; Edenborn, H. M.; Meyer, T. Y. Engineering Hydrolytic Degradation Behavior of Poly (Lactic-Co-Glycolic Acid) through Precise Control of Monomer Sequence. In *Sequence-Controlled Polymers: Synthesis, Self-Assembly, and Properties*; ACS Symposium Series; American Chemical Society, 2014; Vol. 1170, pp 271-286. https://doi.org/10.1021/bk-2014-1170.ch018.

(38) Lin, W.-C.; Sandberg, D. I.; Bhatia, S.; Johnson, M.; Oh, S.; Ragheb, J. Diffuse Reflectance Spectroscopy for in Vivo Pediatric Brain Tumor Detection. *J. Biomed. Opt.* 2010, 15 (6), 061709. https://doi.org/10.1117/1.3505012.

(39) Zhang, H.; Wang, R.; Yang, G.; Xu, Y.; Shao, H. UV-Excitable Fluorescent Poly(Lactic Acid) Fibers. *Polym. Eng. Sci.* 2016, 56 (4), 373-379. https://doi.org/10.1002/pen.24262.

(40) Bhatia, S.; Ragheb, J.; Johnson, M.; Oh, S.; Sandberg, D. I.; Lin, W.-C. The Role of Optical Spectroscopy in Epilepsy Surgery in Children. *Neurosurg. Focus* 2008, 25 (3), E24. https://doi.org/10.3171/FOC/2008/25/9/E24.

(41) R. Hawkins, K.; Yager, P. Nonlinear Decrease of Background Fluorescence in Polymer Thin-Films—a Survey of Materials and How They Can Complicate Fluorescence Detection in MTAS. *Lab. Chip* 2003, 3 (4), 248-252. https://doi.org/10.1039/B307772C.

(42) Altankov, G.; Grinnell, F.; Groth, T. Studies on the Biocompatibility of Materials: Fibroblast Reorganization of Substratum-Bound Fibronectin on Surfaces Varying in Wettability. *J. Biomed. Mater. Res.* 1996, 30 (3), 385-391. https://doi.org/10.1002/(SICI)1097-4636(199603)30: 3<385::AID-JBM13>3.0.CO;2-J.

(43) Rai, R.; Tallawi, M.; Grigore, A.; Boccaccini, A. R. Synthesis, Properties and Biomedical Applications of Poly(Glycerol Sebacate) (PGS): A Review. *Prog. Polym. Sci.* 2012, 37 (8), 1051-1078. https://doi.org/10.1016/j.progpolymsci.2012.02.001.

(44) Sherratt, M. J. Tissue Elasticity and the Ageing Elastic Fibre. *Age* 2009, 31 (4), 305-325. https://doi.org/10.1007/s11357-009-9103-6.

(45) Allen, T. M.; Cullis, P. R. Drug Delivery Systems: Entering the Mainstream. *Science* 2004, 303 (5665), 1818-1822. https://doi.org/10.1126/science.1095833.

(46) Pitt, C. G.; Gratzl, M. M.; Jeffcoat, A. R.; Zweidinger, R.; Schindler, A. Sustained Drug Delivery Systems II: Factors Affecting Release Rates from Poly(ε-Caprolactone) and Related Biodegradable Polyesters. *J. Pharm. Sci.* 68 (12), 1534-1538. https://doi.org/10.1002/jps.2600681219.

(47) Lapidus, H.; Lordi, N. G. Some Factors Affecting the Release of a Water-Soluble Drug from a Compressed Hydrophilic Matrix. *J. Pharm. Sci.* 55 (8), 840-843. https://doi.org/10.1002/jps.2600550818.

(48) Göpferich, A. Mechanisms of Polymer Degradation and Erosion. In *The Biomaterials: Silver Jubilee Compendium*; Williams, D. F., Ed.; Elsevier Science: Oxford, 1996; pp 117-128. https://doi.org/10.1016/B978-008045154-1.50016-2.

(49) Tokiwa, Y.; Ando, T.; Suzuki, T.; Takeda, K. Biodegradation of Synthetic Polymers Containing Ester Bonds. In *Agricultural and Synthetic Polymers*; ACS Symposium Series; American Chemical Society, 1990; Vol. 433, pp 136-148. https://doi.org/10.1021/bk-1990-0433.ch012.

(50) Beenken, K. E.; Bradney, L.; Bellamy, W.; Skinner, R. A.; McLaren, S. G.; Gruenwald, M. J.; Spencer, H. J.; Smith, J. K.; Haggard, W. O.; Smeltzer, M. S. Use of Xylitol To Enhance the Therapeutic Efficacy of Polymethacrylate-Based Antibiotic Therapy in Treatment of Chronic Osteomyelitis. *Antimicrob. Agents Chemother.* 2012, 56 (11), 5839-5844. https://doi.org/10.1128/AAC.01127-12.

(51) Bruggeman, J. P.; Bettinger, C. J.; Langer, R. Biodegradable Xylitol-Based Elastomers: In Vivo Behavior and Biocompatibility. *J. Biomed. Mater. Res. A* 2010, 95 (1), 92-104. https://doi.org/10.1002/jbm.a.32733.

(52) Deepa, K.; Jaisankar, V. Synthesis and Characterisation of Certain Biodegradable Xylitol Based Polyesters. *Asian J. Res. Chem.* 2016, 9 (12), 679. https://doi.org/10.5958/0974-4150.2016.00094.8.

(53) Barbiroli, G.; Lorenzetti, C.; Berti, C.; Fiorini, M.; Manaresi, P. Polyethylene like Polymers. Aliphatic Polyesters of Dodecanedioic Acid: 1. Synthesis and Properties. *Eur. Polym. J.* 2003, 39 (4), 655-661. https://doi.org/10.1016/S0014-3057(02)00280-X.

What is claimed is:

1. A polymer comprising xylitol and dodecanedioic acid, which is a poly(xylitol-dodecanedioic acid) represented by the following general formula:

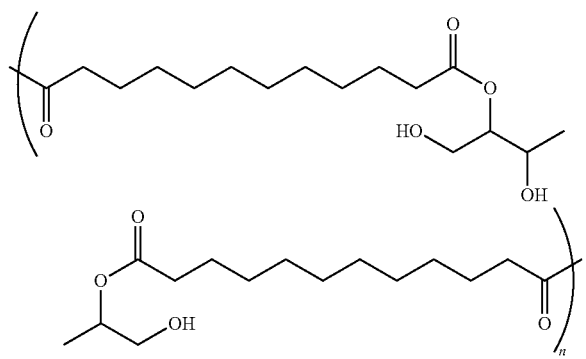

where n is greater than 1.

2. The polymer of claim 1, wherein a molar ratio of xylitol to dodecanedioic acid in the polymer is from 0.5 to less than 2.

3. The polymer of claim 2, which is elastomeric, has an average tensile Young's modulus of 0.11±0.034 MPa, an average elongation at rupture of 66%±17%, and an ultimate tensile strength of 0.065±0.03 MPa.

4. The polymer of claim 1, which has an average Young's modulus of 0.69±0.08 MPa, an average elongation at rupture of 27%±8.1% and an ultimate tensile strength of 0.165±0.04 MPa.

5. The polymer of claim 1, which is fluorescent.

6. A method for synthesizing the polymer of claim 1, said method comprising polymerizing xylitol and dodecanedioic acid to form the polymer which is a poly(xylitol-dodecanedioic acid).

7. The method of claim 6, wherein the polymerizing comprises melt condensation.

8. The method of claim 6, wherein the xylitol and the dodecanedioic acid are combined in a molar ratio of xylitol to dodecanedioic acid from 0.5 to less than 2.

9. The method of claim 6, wherein the polymerizing comprises adding 0.01 wt. % to 2 wt. % of sulfuric acid to a mixture of xylitol and dodecanedioic acid to accelerate a polymerization reaction.

10. A composition comprising the polymer of claim 1 and at least one growth factor bonded to the polymer.

11. The composition of claim 10, wherein the polymer is coated with polydopamine and the growth factor is fibroblast growth factor bonded to the polydopamine.

* * * * *